(12) United States Patent
Yamauchi et al.

(10) Patent No.: US 10,023,760 B2
(45) Date of Patent: Jul. 17, 2018

(54) SEMICARBAZIDE COMPOSITION, METHOD FOR PRODUCING SEMICARBAZIDE COMPOSITION, AQUEOUS POLYMER COMPOSITION AND COMPOSITE

(71) Applicant: ASAHI KASEI CHEMICALS CORPORATION, Tokyo (JP)

(72) Inventors: Toyoaki Yamauchi, Tokyo (JP); Takayuki Miyazaki, Tokyo (JP); Takahiro Itamochi, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 321 days.

(21) Appl. No.: 14/443,288

(22) PCT Filed: Nov. 15, 2013

(86) PCT No.: PCT/JP2013/080908
§ 371 (c)(1),
(2) Date: May 15, 2015

(87) PCT Pub. No.: WO2014/077363
PCT Pub. Date: May 22, 2014

(65) Prior Publication Data
US 2015/0291831 A1    Oct. 15, 2015

(30) Foreign Application Priority Data

Nov. 16, 2012  (JP) ................................. 2012-252603
Nov. 30, 2012  (JP) ................................. 2012-263202

(51) Int. Cl.
| | |
|---|---|
| C09D 133/26 | (2006.01) |
| C07C 281/06 | (2006.01) |
| C08G 18/75 | (2006.01) |
| C08G 18/32 | (2006.01) |
| C08F 220/18 | (2006.01) |
| C09D 133/08 | (2006.01) |
| C09D 163/00 | (2006.01) |
| C08G 59/40 | (2006.01) |

(52) U.S. Cl.
CPC .......... *C09D 133/26* (2013.01); *C07C 281/06* (2013.01); *C08F 220/18* (2013.01); *C08G 18/3231* (2013.01); *C08G 18/755* (2013.01); *C08G 59/4014* (2013.01); *C09D 133/08* (2013.01); *C09D 163/00* (2013.01); *C07C 2601/14* (2017.05)

(58) Field of Classification Search
CPC .................................................. C09D 133/26
See application file for complete search history.

(56) References Cited

U.S. PATENT DOCUMENTS

| | | | |
|---|---|---|---|
| 5,098,466 A * | 3/1992 | Anderson | A01N 47/34 504/235 |
| 5,472,996 A | 12/1995 | Hayashi et al. | |
| 5,714,615 A * | 2/1998 | Powers | A61K 31/44 546/291 |
| 5,880,312 A | 3/1999 | Nakabayashi et al. | |
| 6,893,683 B1 | 5/2005 | Hesselmans et al. | |
| 2001/0018170 A1* | 8/2001 | Oyamada | G03C 1/49809 430/620 |
| 2006/0287260 A1 | 12/2006 | Manoharan et al. | |
| 2009/0099298 A1 | 4/2009 | Yukawa | |

FOREIGN PATENT DOCUMENTS

| | | |
|---|---|---|
| CN | 101407688 A | 4/2009 |
| GB | 2453669 A | 4/2009 |
| JP | 46-20053 Y1 | 6/1971 |
| JP | 57-3850 A | 1/1982 |
| JP | 57-3857 A | 1/1982 |
| JP | 58-96643 A | 6/1983 |
| JP | 4-249587 A | 9/1992 |
| JP | 6-287457 A | 10/1994 |
| JP | 10-298158 A | 11/1998 |
| JP | 2001-164126 A | 6/2001 |
| JP | 2003-510431 A | 3/2003 |
| JP | 2005-29515 A | 2/2005 |
| JP | 2005-42023 A | 2/2005 |
| JP | 2005-350580 A | 12/2005 |
| JP | 4033518 B2 | 11/2007 |
| JP | 2008-504840 A | 2/2008 |
| WO | WO 96/01252 A1 | 1/1996 |

OTHER PUBLICATIONS

Supplementary European Search Report for European Application No. 13855684.0, dated Nov. 4, 2015.
International Preliminary Report on Patentability and English translation of the Written Opinion of the International Searching Authority (Forms PCT/IB/338, PCT/IB/373 and PCT/ISA/237), dated May 28, 2015, for International Application No. PCT/JP2013/080908.
International Search Report (Form PCT/ISA/210), dated Feb. 10, 2014, for International Application No. PCT/JP2013/080908.

* cited by examiner

*Primary Examiner* — Megan McCulley
(74) *Attorney, Agent, or Firm* — Birch, Stewart, Kolasch & Birch, LLP

(57) ABSTRACT

Provided is a semicarbazide composition comprising: a semicarbazide compound (A) having an amino group and a semicarbazide group; a semicarbazide compound (B-1) having a structure with a semicarbazide group substituted for the amino group of the semicarbazide compound (A); a semicarbazide compound (B-2) as a dimer of the semicarbazide compound (B-1); and a semicarbazide compound (B-3) as a trimer of the semicarbazide compound (B-1); the semicarbazide composition having an analysis area ratio (a) of 0.008% or more and 2% or less.

2 Claims, 5 Drawing Sheets

SEMICARBAZIDE COMPOSITION, METHOD FOR PRODUCING SEMICARBAZIDE COMPOSITION, AQUEOUS POLYMER COMPOSITION AND COMPOSITE

TECHNICAL FIELD

The present invention relates to a semicarbazide composition, the method for producing a semicarbazide composition, and an aqueous polymer composition and a composite.

BACKGROUND ART

In recent years, aqueous polymer compositions have attracted attention as material for converting to a waterborne system from an organic solvent system in the coating field. Waterborne paints produced from aqueous polymer compositions, however, still have not exhibited sufficient physical properties such as water resistance, stain resistance, and hardness in comparison with organic solvent-based paints. In the description here, an aqueous polymer composition indicates the polymer dissolved and/or dispersed in water.

In this field, in order to improve physical properties of a coating film, a functional group is generally introduced in the polymer of aqueous polymer composition to make cross-linkable, so that a coating film composed of a cross-linked product of polymer (hereinafter referred to as cross-linked coating film) can be formed.

As an aqueous polymer composition to form a cross-linked coating film, the demand for cold-curing, a cold-curing, one-pack type which is a mixture of a cross-linking agent and a polymer, capable of forming a cross-linked coating film in association with evaporation of an aqueous medium without heating when applied is highly demanded. In response to the demand, a hydrazone cross-linked waterborne polymer dispersions with use of a dehydration condensation reaction between a carbonyl group and a hydrazide group have attracted attention in recent years.

In the description here, "cold-curing, one-pack type" indicates a paint which forms a coating film at 25° C., having storage stability. In determination of storage stability, for example, when a coating film formed from a paint applied to a substrate after storage at 50° C. for 2 weeks has water resistance, stain resistance, and hardness similar to those of a coating film formed from the paint before the storage, the paint is considered to have storage stability.

For example, a method for providing a waterborne paint having both of the cold-curing ability and the storage stability, excellent in hardness, stain resistance, etc., by adding dicarboxylic acid dihydrazide as a cross-linking agent to a carbonyl group-containing waterborne polymer dispersion, has been proposed (Patent Literature 1 to 6). In this method, however, dicarboxylic acid dihydrazide for use as cross-linking agent is hydrolyzed during storage of a waterborne paint, resulting in lowered cross-linking ability (curing properties). In other words, the ability to form a cross-linked coating film having excellent hardness, stain resistance, and solvent resistance is lowered with time. Furthermore, in the above literature, a compound having low compatibility with a carbonyl group-containing copolymer and high hydrophilic properties such as adipic acid dihydrazide is used as dicarboxylic acid dihydrazide, causing a disadvantage that the produced cross-linked coating film has markedly inferior water resistance.

Since the curing properties of a conventional waterborne paint containing a conventional cross-linking agent and a carbonyl group-containing copolymer deteriorate with time as described above, the composition cannot exhibit adequate cross-linking performance when applied to a substrate surface. Furthermore, use of dicarboxylic acid dihydrazide having low compatibility with a carbonyl group-containing copolymer as cross-linking agent causes a problem that the produced coating film by application has markedly inferior water resistance.

In Patent Literature 7 and 8, at least one selected from the group consisting of a semicarbazide derivative and a terminal-blocked product thereof obtained by a reaction between a polyisocyanate having 3 to 20 isocyanate groups and hydrazine or a derivative thereof, or a mixture of a non-terminal-blocked product and a terminal-blocked product thereof; and a semicarbazide mixture including at least one selected from the group consisting of the semicarbazide derivative and a terminal-blocked product thereof, and at least one selected from the group consisting of a hydrophilic group-containing compound and a terminal-blocked product thereof is proposed as a cross-linking agent. The semicarbazide mixture, however, includes a large amount of compounds with terminal amino groups as by-products, having a disadvantage of yellowing easily caused by a basic substance.

In Patent Literature 9, in addition to the auto-oxidation in a mixed system of an alkyd type emulsion and a styrene-acrylic emulsion containing large amounts of carboxylic acid, a styrene-acrylic emulsion ring-opening epoxy group is supported as a second cross-linking agent for combination use of the cross-linking reaction with dicarboxylic acid dihydrazide. The water resistance of the coating film of acrylic emulsion containing large amounts of carboxylic acid, however, is not satisfactory.

In Patent Literature 10, in order to improve the water resistance of a coating film for exhibiting the stain resistance, use of isophorone disemicarbazide as cross-linking agent in a waterborne polymer dispersion formed of copolymer which contains a carbonyl group having a high Tg (glass transition temperature) is disclosed. The combination of a polymer having a high Tg and isophorone disemicarbazide, however, has a disadvantage of incapability of film formation even with use of a coalescing agent, due to hardening in a film formation process.

Though isophorone disemicarbazide is disclosed in Patent Literature 11, a semicarbazide composition having a large amount of compounds having terminal amino groups is obtained due to use of an excessive amount of hydrazine during reaction, so that use of the semicarbazide composition as cross-linking agent causes a problem that the produced cross-linked coating film easily causes yellowing when immersed in an aqueous alkali solution. Furthermore, the production method described in Patent Literature 11, a step for removing remaining hydrazine is required.

CITATION LIST

Patent Literature

Patent Literature 1: Japanese Patent Publication No. 46-20053
Patent Literature 2: Japanese Patent Application Laid-Open No. 57-3850
Patent Literature 3: Japanese Patent Application Laid-Open No. 57-3857
Patent Literature 4: Japanese Patent Application Laid-Open No. 58-96643

Patent Literature 5: Japanese Patent Application Laid-Open No. Hei-4-249587

Patent Literature 6: Japanese Patent Application Laid-Open No. Hei-6-287457

Patent Literature 7: International Publication No. WO 96/01252

Patent Literature 8: Japanese Patent Application Laid-Open No. 2001-164126

Patent Literature 9: Japanese Patent Application Laid-Open No. 2008-504840

Patent Literature 10: Japanese Patent Application Laid-Open No. 2005-350580

Patent Literature 11: Japanese Patent No. 4033518

SUMMARY OF INVENTION

Technical Problem

An object of the present invention is to provide a semicarbazide composition capable of improving the hardness, the stain resistance, the alkali yellowing resistance, and the like of a waterborne coating film with a small amount of addition, and a method for producing the same. Another object of the present invention is to provide an aqueous polymer composition including the semicarbazide composition, and a composite having a coating film obtained from the aqueous polymer composition.

An aspect of the present invention relates to the following.

[1]

A semicarbazide composition comprising:

a semicarbazide compound (A) having an amino group and a semicarbazide group;

a semicarbazide compound (B-1) having a structure with a semicarbazide group substituted for the amino group of the semicarbazide compound (A);

a semicarbazide compound (B-2) as a dimer of the semicarbazide compound (B-1); and a semicarbazide compound (B-3) as a trimer of the semicarbazide compound (B-1);

the semicarbazide composition having an analysis area ratio (a) represented by the following expression (a) of 0.008% or more and 2% or less:

[Expression 1]

$$\text{Analysis area ratio (a)} = S_A/(S_A + S_{B-1} + S_{B-2} + S_{B-3}) \times 100 \quad \text{(a)}$$

wherein $S_A$, $S_{B-1}$, $S_{B-2}$, and $S_{B-3}$ represent the peak areas of peaks derived from the semicarbazide compound (A), the semicarbazide compound (B-1), the semicarbazide compound (B-2), and the semicarbazide compound (B-3), respectively, in a chromatogram obtained by high performance liquid chromatography analysis of the semicarbazide composition.

[2]

The semicarbazide composition according to [1], wherein:

the semicarbazide compound (A) is a compound represented by the following formula (1-1) or the following formula (1-2); and the semicarbazide compound (B-1) is a compound represented by the following formula (2-1).

[Chemical Formula 1]

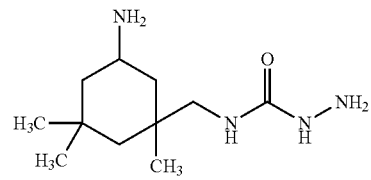
(1-1)

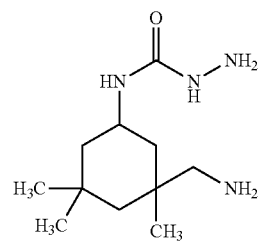
(1-2)

[Chemical Formula 2]

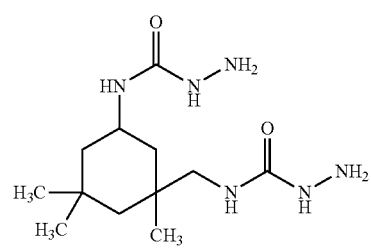
(2-1)

[3]

The semicarbazide composition according to [2], wherein:

the semicarbazide compound (B-2) is a compound represented by the following formula (2-2), and the semicarbazide compound (B-3) is a compound represented by the following formula (2-3):

[Chemical Formula 3]

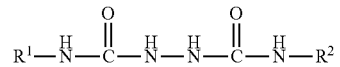
(2-2)

[Chemical Formula 4]

(2-3)

wherein $R^1$, $R^2$, $R^3$, and $R^4$ each independently represent a monovalent group represented by the following formula (2-a) or the following formula (2-b), and $R^5$ represents a divalent group represented by the following formula (2-c):

[Chemical Formula 5]

(2-a)

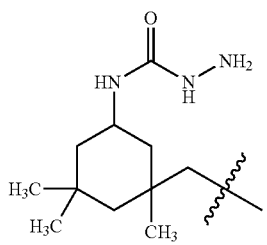

[Chemical Formula 6]

(2-b)

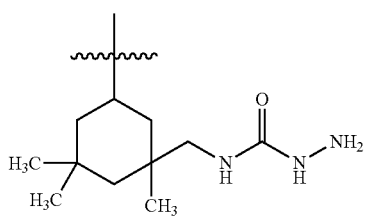

[Chemical Formula 7]

(2-c)

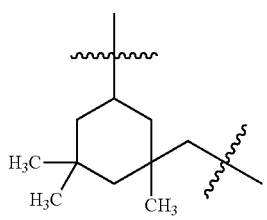

[4]

The semicarbazide composition according to any of [1] to [3], wherein the semicarbazide composition is a composition produced by reacting a compound (C) having two or more isocyanate groups in the molecule with hydrazine or a hydrazine derivative.

[5]

The semicarbazide composition according to [4], wherein the compound (C) is a compound represented by the following formula (4):

[Chemical Formula 8]

(4)

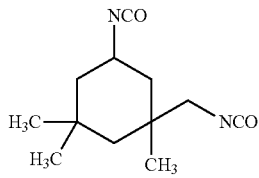

[6]

The semicarbazide composition according to any of [1] to [5], wherein the analysis area ratio (b-1) represented by the following expression (b-1) is 50% or more and 99% or less, the analysis area ratio (b-2) represented by the following expression (b-2) is 0.9% or more and 30% or less, and the analysis area ratio (b-3) represented by the following expression (b-3) is 0.01% or more and 20% or less:

[Expression 2]

$$\text{Analysis area ratio (b-1)}=S_{B-1}/(S_A+S_{B-1}+S_{B-2}+S_{B-3})\times 100 \quad \text{(b-1)}$$

$$\text{Analysis area ratio (b-2)}=S_{B-2}/(S_A+S_{B-1}+S_{B-2}+S_{B-3})\times 100 \quad \text{(b-2)}$$

$$\text{Analysis area ratio (b-3)}=S_{B-3}/(S_A+S_{B-1}+S_{B-2}+S_{B-3})\times 100 \quad \text{(b-3)}$$

[7]

A method for producing the semicarbazide composition according to any of [1] to [6], comprising a reaction step of reacting a compound (C) having two or more isocyanate groups in the molecule with hydrazine or a hydrazine derivative in a solvent to obtain the semicarbazide composition.

[8]

The method according to [7], wherein the ratio of the number of moles of the hydrazine or hydrazine derivative to the number of moles of the isocyanate groups of the compound (C) is 0.7 to 5 in the reaction step.

[9]

The method according to [7] or [8], wherein in the reaction step, the solvent contains a water-soluble organic solvent and a water-insoluble solvent; and the amount of the water-insoluble solvent relative to the total amount of the water-soluble organic solvent and the water-insoluble solvent is 20 mass % or more.

[10]

An aqueous solution comprising the semicarbazide composition according to any of [1] to [6] in an amount of 5 mass % or more.

[11]

An aqueous polymer composition for use as a waterborne paint or a waterborne coating material comprising:

the semicarbazide composition according to any of [1] to [6]; and a polymer reactive with a semicarbazide group to form a cross-linked structure.

[12]

A composite comprising a substrate and a coating film formed of the aqueous polymer composition according to [11].

[13]

An aqueous polymer composition comprising a cross-linking agent and a waterborne polymer dispersion;

the cross-linking agent comprising the semicarbazide composition according to any of [1] to [6]; and the waterborne polymer dispersion comprising at least one cross-linkable polymer having a glass transition temperature Tg of lower than 80° C., selected from the group consisting of a water-soluble or water-dispersible polycarbonyl compound having a number average molecular weight of 1000 to 100000, and a water-soluble or water-dispersible polyepoxy compound having a number average molecular weight of 1000 to 100000.

[14]

The aqueous polymer composition according to [13], wherein the waterborne polymer dispersion is produced by emulsion polymerization.

[15]

A coating film formed from the aqueous polymer composition according to [13] or [14], comprising a cross-linked product of the cross-linkable polymer.

Advantageous Effects of Invention

The present invention provides a semicarbazide composition capable of improving the hardness, the stain resistance, the alkali yellowing resistance, and the like of a waterborne coating film with a small amount of addition, and a method for producing the same. The present invention also provides an aqueous polymer composition including the semicarbazide composition, and a composite having a coating film obtained from the aqueous polymer composition.

DESCRIPTION OF EMBODIMENTS

Figure 1:
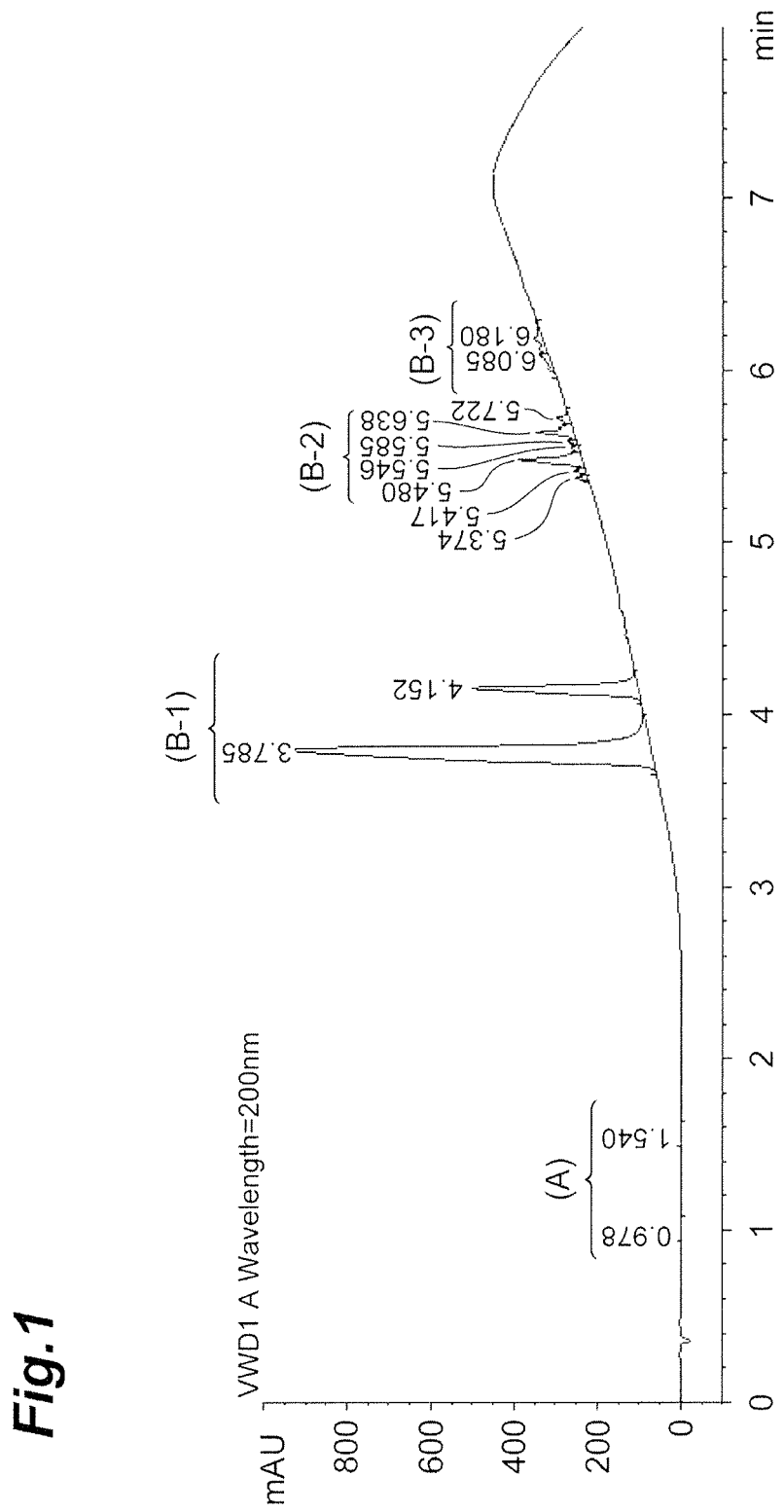
FIG. 1 is a chart showing the LC/MS analysis results of the semicarbazide composition obtained in Example 1-1.

The preferred embodiments of the present invention are described in detail in the following. The present invention, however, is not limited to the following embodiments.

(Semicarbazide Composition)

The semicarbazide composition of the present embodiments includes a semicarbazide compound having an amino group and a semicarbazide group (hereinafter referred to as "semicarbazide compound (A)"), a semicarbazide compound having a structure with semicarbazide group substituted for the amino group of the semicarbazide compound (A) (hereinafter referred to as "semicarbazide compound (B-1)"), a dimer of the semicarbazide compound (B-1) (hereinafter referred to as "semicarbazide compound (B-2)"), and a trimer of the semicarbazide compound (B-1) (hereinafter referred to as "semicarbazide compound (B-3)").

The semicarbazide composition of the present embodiments has an analysis area ratio (a) represented by the following expression (a) of 0.008% or more and 2% or less.

[Expression 3]

Analysis area ratio (a)=$S_A/(S_A+S_{B-1}+S_{B-2}+S_{B-3})\times 100$    (a)

In the expression, $S_A$ represents the peak area of the peak derived from semicarbazide compound (A) in a chromatogram obtained by high performance liquid chromatography analysis of the semicarbazide composition, $S_{B-1}$ represents the peak area of the peak derived from semicarbazide compound (B-1) in the chromatogram, $S_{B-2}$ represents the peak area of the peak derived from semicarbazide compound (B-2) in the chromatogram, and $S_{B-3}$ represents the peak area of the peak derived from semicarbazide compound (B-3) in the chromatogram.

With an analysis area ratio (a) of 2% or less, the alkali yellowing resistance of the cross-linked coating film made from a semicarbazide composition can be remarkably improved. With an analysis area ratio (a) of 0.008% or more, the hydrolysis resistance of the cross-linked coating film made from a semicarbazide composition is remarkably improved.

The cross-linking reaction of the semicarbazide group is a reversible reaction in the presence of water, while the cross-linking reaction of the amino group of a semicarbazide compound (A) is an irreversible reaction, so that a cross-linked coating film including a large amount of cross-linked structures formed by amino groups has excellent hydrolysis resistance. On the other hand, the presence of a large amount of amino groups in a cross-linked coating film causes a problem of easy yellowing when the coating film is immersed in an aqueous alkali solution. In the present embodiments, the presence of semicarbazide compound (A) in an appropriate range in a semicarbazide composition enables formation of a cross-linked coating film excellent in both of the alkali yellowing resistance and the hydrolysis resistance.

From the viewpoint of further improvement of the properties of a cross-linked coating film made from a semicarbazide composition (in particular, alkali yellowing resistance), the analysis area ratio (a) is preferably 0.008% or more and 1% or less, more preferably 0.01% or more and 0.5% or less.

In order to have an analysis area ratio (a) of 0.008% or more and 2% or less, it is important to suppress the formation of semicarbazide compound (A) in the production step of the semicarbazide composition, due to difficulty in removal of semicarbazide compound (A) from a conventional semicarbazide composition by an operation such as extraction or separation.

The semicarbazide compound (A) is a compound having an amino group and a semicarbazide group. The semicarbazide compound (A) may have two or more amino groups, or may have two or more semicarbazide groups. The semicarbazide group is a group represented by the following formula (10).

[Chemical Formula 9]

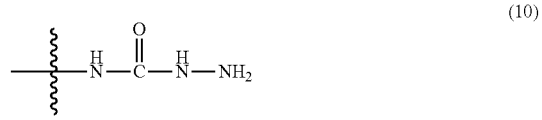

(10)

The semicarbazide compound (B-1) is a compound having a structure with semicarbazide groups substituted for all the amino groups of the semicarbazide compound (A). In other words, the semicarbazide compound (B-1) is a compound having no amino group and at least two semicarbazide groups.

The semicarbazide composition has an analysis area ratio (b-1) represented by the following expression (b-1) of preferably 50% or more and 99% or less. In the expression, $S_A$, $S_{B-1}$, $S_{B-2}$, and $S_{B-3}$ are the same as defined above.

[Expression 4]

Analysis area ratio (b-1)=$S_{B-1}/(S_A+S_{B-1}+S_{B-2}+S_{B-3})\times 100$    (b-1)

The semicarbazide compound (B-2) is a dimer of the semicarbazide compound (B-1). It can be said that the semicarbazide compound (B-2) is a compound of two semicarbazide compounds (B-1) coupled by a condensation reaction of semicarbazide groups, having a bond represented by the following formula (11). Alternatively it can be said that the semicarbazide compounds (B-2) is a compound having two or more semicarbazide groups and one bond represented by the following formula (11).

[Chemical Formula 10]

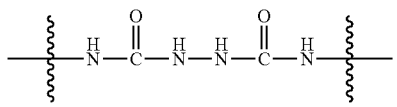

(11)

The semicarbazide composition has an analysis area ratio (b-2) represented by the following expression (b-2) of preferably 0.9% or more and 30% or less. In the expression, $S_A$, $S_{B-1}$, $S_{B-2}$, and $S_{B-3}$ are the same as defined above. With an analysis area ratio (b-2) in the range, the resulting coating film can be further toughened.

[Expression 5]

$$\text{Analysis area ratio (b-2)} = S_{B-2}/(S_A+S_{B-1}+S_{B-2}+S_{B-3}) \times 100 \quad \text{(b-2)}$$

The semicarbazide compound (B-3) is a trimer of the semicarbazide compound (B-1). It can be said that the semicarbazide compound (B-3) is a compound of three semicarbazide compounds (B-1) bonded by a condensation reaction of semicarbazide groups, or a compound of the semicarbazide compound (B-2) and the semicarbazide compound (B-1) bonded by a condensation reaction of semicarbazide groups. Alternatively it can be said that the semicarbazide compound (B-2) is a compound having two or more semicarbazide groups and two bonds represented by formula (11).

The semicarbazide composition has an analysis area ratio (b-3) represented by the following expression (b-3) of preferably 0.01% or more and 20% or less. In the expression, $S_A$, $S_{B-1}$, $S_{B-2}$, and $S_{B-3}$ are the same as defined above. With an analysis area ratio (b-3) in the range, the resulting coating film can be further toughened.

[Expression 6]

$$\text{Analysis area ratio (b-3)} = S_{B-3}/(S_A+S_{B-1}+S_{B-2}+S_{B-3}) \times 100 \quad \text{(b-3)}$$

In a semicarbazide composition, the total content of the semicarbazide compound (A), the semicarbazide compound (B-1), the semicarbazide compound (B-2), and the semicarbazide compound (B-3) is preferably 90 mass % or more, more preferably 95 mass % or more, furthermore preferably 98 mass % or more, based on the total amount of the semicarbazide composition.

Although the semicarbazide composition may contain high molecular weight components, i.e. the tetramer or more of the semicarbazide compound (A), such high molecular weight components are insoluble in water in many cases, so that the content of the high molecular weight components is preferably small. For example, the content of the high molecular weight components is preferably 1.0 mass % or less, more preferably 0.5 mass % or less, furthermore preferably 0.1 mass % or less, based on the total amount of the semicarbazide composition.

The high performance liquid chromatography analysis of a semicarbazide composition may be performed with an LC/MS (Liquid Chromatograph Mass Spectrometer) by the following method.

(Analysis Method)

A semicarbazide composition is freeze-dried and then a 10 mg/ml of aqueous solution is prepared. Subsequently, the solution is centrifuged at 12000 rpm for 10 minutes with a centrifugal separator made by Hsiangtai Machinery Industry (MODEL MCD-2000) and the supernatant thereof is measured by LC/MS. The device configuration of the LC/MS includes an "AGILENT, 1100 series" as LC and "THERMO ELECTRON, LCQ" as MS. Each of the peaks obtained by the measurement is identified by MS, and the peak area of each peak is obtained from the area value of the absorbance at 200 nm in the ultraviolet-visible detector in LC.

The measurement conditions for LC/MS are shown in the following. The LC conditions are shown in the first place. By using an LC column of Phenomenex, Kinetex 2.6u C18-XB 100A (2.1 mm I.D.×50 mm), at a column oven temperature of 40° C., with two types of solutions, i.e. a 0.1% formic acid aqueous solution (a) and a 0.1% formic acid containing methanol solution (b) as the solvents for the mobile phase, the liquid composition is linearly changed from 98% of liquid (a) to 100% of liquid (b) in 5 minutes, and then brought back to 98% of liquid (a) again in 5.1 minutes, so that the liquid composition with 98% of liquid (a) is maintained for 12 minutes. The flow rate of the mobile phase is set to 0.4 ml/min, and the sample injection volume is set to 1 µl.

The wavelength of the ultraviolet-visible absorption detector attached to LC is set to 200 nm. The wavelength of the detector can be appropriately changed according to the substance to be handled, and a wavelength of 200 nm is preferred for the semicarbazide composition obtained by the reaction of isophorone diisocyanate with hydrazine.

The MS conditions are shown in the second place. In positive mode of ESI (Electrospray Ionization), scanning is performed with a mass-to-charge ratio (m/z) in the range of 150 to 1000.

Each of the semicarbazide compound (A), the semicarbazide compound (B-1), the semicarbazide compound (B-2), and the semicarbazide compound (B-3) may include a plurality of isomers. In this case, the sum of the peak areas of a peak group including a plurality of isomers is assumed to be the peak area for each of the semicarbazide compound (A), the semicarbazide compound (B-1), the semicarbazide compound (B-2), and the semicarbazide compound (B-3).

For example, in the following aspects, each of the compounds represented by formulas (1-1), (1-2), (2-1), (2-2) and (2-3) may have a plurality of isomers. On this occasion, the peak area of the semicarbazide compound (A) is the sum of the peak areas of the group of compounds represented by formula (1-1) or (1-2), the peak areas of the semicarbazide compound (B-1) is the sum of the peak areas of the group of compounds represented by formula (2-1), the peak area of the semicarbazide compound (B-2) is the sum of the peak areas of the group of compounds represented by formula (2-2), and the peak area of the semicarbazide compound (B-3) is the sum of the peak areas of the group of compounds represented by formula (2-3).

Even a semicarbazide composition contained in the aqueous polymer composition of a paint or the like can be analyzed, for example, by the following method. First, the paint is diluted with water, and subjected to centrifugal separation for sampling the supernatant. After precipitation of latex by ultracentrifugation, the supernatant is passed through a dialysis membrane (Molecular weight cut off: 10000). Subsequently the liquid passing through the dialysis membrane is concentrated into a concentrate, which is analyzed by LC/MS so as to obtain the peak areas of the peaks derived from the semicarbazide compounds (A), (B-1), (B-2), and (B-3). In order to further detect the semicarbazide compound (A) immobilized in latex, the latex precipitated by ultracentrifugation is re-dispersed in water. The re-dispersed solution and a cation exchange polymer are mixed for adsorption of alkali components, and the cation exchange polymer is filtered and substituted with a diluted KOH aqueous solution. The aqueous solution is analyzed by LC/MS for detection of the semicarbazide compound (A) immobilized in latex.

Subsequently, one preferred aspect of the semicarbazide composition is described in the following. In the present aspect, the semicarbazide compound (A) is a compound represented by the following formula (1-1) or the following formula (1-2), and the semicarbazide compound (B-1) is a compound represented by the following formula (2-1).

[Chemical Formula 11]

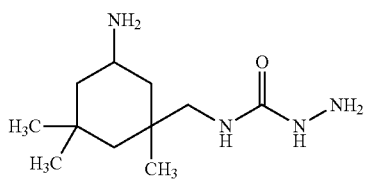

(1-1)

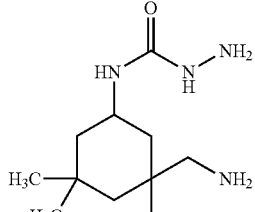

(1-2)

[Chemical Formula 12]

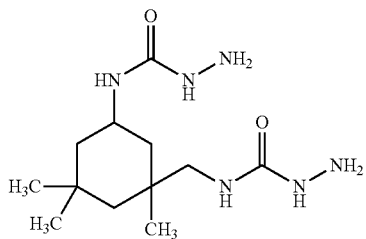

(2-1)

Further, in the present aspect, the semicarbazide compound (B-2) is a compound represented by the following formula (2-2), and the semicarbazide compound (B-3) is a compound represented by the following formula (2-3).

[Chemical Formula 13]

$$R^1-\underset{H}{N}-\underset{}{\overset{O}{\overset{\|}{C}}}-\underset{H}{N}-\underset{H}{N}-\underset{}{\overset{O}{\overset{\|}{C}}}-\underset{H}{N}-R^2$$

(2-2)

[Chemical Formula 14]

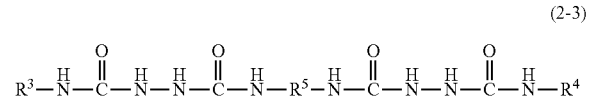

(2-3)

In the formulas, $R^1$, $R^2$, $R^3$, and $R^4$ each independently represent a monovalent group represented by the following formula (2-a) or the following formula (2-b), and $R^5$ represents a divalent group represented by the following formula (2-c).

[Chemical Formula 15]

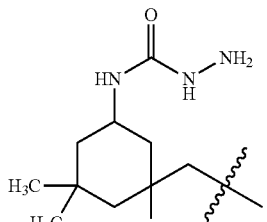

(2-a)

[Chemical Formula 16]

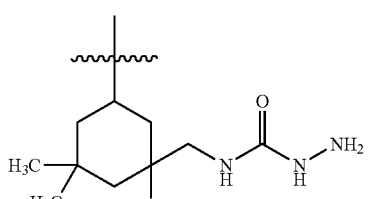

(2-b)

[Chemical Formula 17]

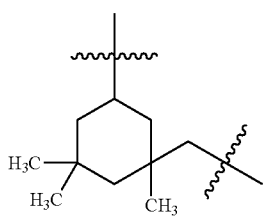

(2-c)

The semicarbazide composition of the present aspect is excellent particularly in water-solubility, being suitably used as a cross-linking agent for a waterborne paint, in particular. Further, the semicarbazide composition of the present aspect with an analysis area ratio (a) in the specific range more remarkably exhibits the effect of the present invention.

A semicarbazide composition can be obtained by, for example, reacting a compound having two or more isocyanate groups in the molecule (hereinafter referred to as "isocyanate compound (C)") with hydrazine or a hydrazine derivative (hereinafter referred to as "hydrazines (D)").

On this occasion, the semicarbazide compound (A) is a compound in which a portion of isocyanate groups of the isocyanate compound (C) is converted to amino groups and another portion is converted into semicarbazide groups. The semicarbazide compound (B-1) is a compound in which the entire isocyanate groups of the isocyanate compound (C) are converted to semicarbazide groups.

Examples of the isocyanate compound (C) include a diisocyanate compound having two isocyanate groups in the molecule and a polyisocyanate compound having three or more isocyanate groups in the molecule, Examples of the diisocyanate compound include an alkylene diisocyanate such as N-hexamethylene diisocyanate (HDI); a cycloalkylene diisocyanate such as 4,4'-methylene bis(cyclohexyl)diisocyanate (hydrogenated MDI), isophorone diisocyanate (IPDI), and dimethyl cyclohexane diisocyanate (hydrogenated XDI); an arylene diisocyanate such as 2,4-tolylene diisocyanate, 2,6-tolylene diisocyanate and a mixture thereof (TDIs), diphenylmethane-4,4'-diisocyanate (MDI), naphthalene-1,5-diisocyanate (NDI), 3,3-dimethyl-4,4-diphenylene diisocyanate (TODI), crude TDIs, polymethylene polyphenyl diisocyanate, crude MDI, and phenylene diisocyanate; and an aralkylene diisocyanate such as xylylene diisocyanate (XDI); which may be used in combination.

Examples of the polyisocyanate compound include trimer to 20-mers oligomerized from a diisocyanate compound by forming a biuret bond, a urea bond, an isocyanurate bond, a urethane bond, an allophanate bond, or a uretdione bond. For further information on the method for producing these polyisocyanate compounds and the bonds in polyisocyanate compounds, refer to, for example, "Polyurethane Handbook" edited by G. Oertel (Hauser Publishers, Germany, 1985).

As the isocyanate compound (C), diisocyanate compounds are preferred, and isophorone diisocyanate is particularly preferred. Isophorone diisocyanate is a compound represented by the following formula (4), and the semicarbazide composition obtained from isophorone diisocyanate can be particularly suitably used as a cross-linking agent for a waterborne paint or the like, with high water-solubility.

[Chemical Formula 18]

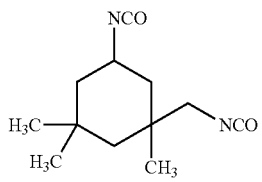

(4)

Examples of the hydrazines (D) include hydrazine and a hydrate thereof; a monoalkyl-substituted hydrazine compound such as monomethyl hydrazine, monoethyl hydrazine, and monobutyl hydrazine; a dihydrazine compound such as ethylene-1,2-dihydrazine, propylene-1,3-dihydrazine, and butylene-1,4-dihydrazine; a dicarboxylic acid dihydrazide such as oxalic acid dihydrazide, malonic acid dihydrazide, succinic acid dihydrazide, glutaric acid dihydrazide, adipic acid dihydrazide, sebacic acid dihydrazide, maleic acid dihydrazide, fumaric acid dihydrazide, itaconic acid dihydrazide, isophthalic acid dihydrazide, and phthalic acid dihydrazide; a reaction product of hydrazine and a compound having two or more carboxyl groups such as a tricarboxylic acid trihydrazide such as trimellitic trihydrazide, and a mixture thereof.

In the reaction of the isocyanate compound (C) with the hydrazines (D) (hereinafter referred to as "reaction into semicarbazide" in some cases), the ratio of the amount used $X_D$ (mol) of the hydrazines (D) to the total number $X_C$ (mol) of the isocyanate groups of the isocyanate compound (C), i.e. $X_D/X_C$, is preferably 0.7 to 2.50, more preferably 0.75 to 1.19, furthermore preferably 0.80 to 0.99. As the ratio $X_D/X_C$ increases, the basicity of the reaction system is enhanced, so that isocyanate groups tend to be easily converted to amino groups. With a ratio $X_D/X_C$ in the range, a sufficient reaction rate can be obtained, and the conversion of isocyanate groups to amino groups can be sufficiently suppressed. With a ratio $X_D/X_C$ in the range, the hydrazines (D) hardly remain unreacted, resulting in another advantage that the operation to remove the unreacted hydrazines (D) is unnecessary after the reaction.

The reaction into semicarbazide may be performed using a suitable solvent, on an as needed basis. Examples of the solvent include water; alcohols such as methanol, ethanol, isopropanol, 1-butanol, 2-butanol butyl cellosolve, propylene glycol monopropyl ether, and octyl alcohol; esters such as methyl acetate, ethyl acetate and butyl acetate; ethers such as diethyl ether, tetrahydrofuran, dioxane, dimethoxyethane, and diethylene glycol dimethyl ether; ketones such as acetone, methyl ethyl ketone, methyl isobutyl ketone; amides such as dimethylformamide and dimethylacetamide; chlorinated solvents such as methylene chloride, chloroform, and carbon tetrachloride; and nonpolar solvents such as toluene, xylene, hexane, cyclohexane, and petroleum ether. Among them, ketones cause dehydration condensation with a semicarbazide compound, so that hydrolysis with water is required after reaction.

The solvent for use in the reaction into semicarbazide is not necessarily a solvent which dissolves both the isocyanate compound (C) and the hydrazines (D), because the reaction can be performed with forced agitation in a reaction vessel.

Alternatively, a water-soluble organic solvent and a water-insoluble organic solvent may be used in combination as the solvent, with a ratio of the amount of water-insoluble organic solvent to the total amount of solvent at the end of the reaction of preferably 20 mass % or more, more preferably 30 mass % or more, furthermore preferably 45 mass % or more. The ratio may be 100 mass %.

Examples of the water-soluble organic solvent include the alcohols, the esters, the ethers, the ketones, and the amides described above. Examples of the water-insoluble organic solvent include the chlorinated solvents and the non-polar solvents described above.

Although the reaction into semicarbazide may be performed at any temperature, the temperature is preferably 0 to 100° C., more preferably 0 to 50° C., from the viewpoint of sufficiently suppressing the formation of the dimer semicarbazide compound (B-2) and the trimer semicarbazide compound (B-3) as byproducts so as to increase the yield of the semicarbazide compound (B-1).

Although the reaction into semicarbazide may be performed by any method for mixing the isocyanate compound (C) and the hydrazines (D), a reaction method of adding the isocyanate compound (C) or the solution thereof into the hydrazines (D) or the solution thereof; a reaction method of simultaneously adding the isocyanate compound (C) or the solution thereof and the hydrazines (D) or the solution thereof into a solvent; or a reaction method of simultaneously adding the isocyanate compound (C) or the solution thereof into the hydrazines (D) or the solution thereof are preferred from the viewpoint of further suppressing side reactions.

After the reaction into semicarbazide, the semicarbazide composition having an analyzed area ratio (a) in the range can be obtained through, for example, extraction operation or the like from the reaction liquid.

Examples of the extraction operation include distillation, crystallization, and column chromatography. Among them, an extraction operation requiring no heating (e.g. crystallization, column chromatography, extraction with water from suspension in organic solvent) is preferred to avoid yellowing by heating.

The solvent for use in crystallization is not particularly limited as long as the solvent is nonreactive with the semicarbazide composition, and examples thereof include alcohols such as methanol, ethanol, isopropanol, 1-butanol, 2-butanol butyl cello solve, and propylene glycol monopropyl ether; esters such as methyl acetate, ethyl acetate and butyl acetate; ethers such as diethyl ether, tetrahydrofuran, dioxane, dimethoxyethane, diethylene glycol dimethyl ether; and amides such as dimethylformamide and dimethylacetamide. Among them, ethers are preferred, with the solubility of the semicarbazide compound (B-1) being greatly different depending on temperature; and dioxane, tetrahydrofuran, and dimethoxyethane are more preferred.

In the method of extraction with water from suspension in organic solvent, an organic solvent hardly dissolving the semicarbazide compound (B-1) can be used, and examples of the organic solvent for suitable use include non-polar solvents such as toluene, xylene, hexane, cyclohexane, and petroleum ether.

Alternatively, a semicarbazide composition may be suitably obtained by reacting the isocyanate compound (C) and the hydrazines (D) with forced agitation, suspending water after completion of the reaction, and then extracting the semicarbazide composition with water.

The semicarbazide composition obtained by the extraction operation may be directly used or may be diluted with a solvent for use. Though examples of the diluting solvent include water; alcohols such as methanol, ethanol, isopropanol, and butanol; and a coalescing agent such as butyl cellosolve, CS-12 (made by JNC Corporation), and butyl carbitol; water is preferred to reduce volatile organic solvent.

The semicarbazide composition can be suitably used as a cross-linking agent for a polymer capable of forming a cross-linked structure by reacting with semicarbazide groups. More specifically, the semicarbazide composition can be suitably used as a cross-linking agent to be added to an aqueous polymer composition containing a polymer capable of forming a cross-linked structure by reacting with semicarbazide groups.

The semicarbazide composition can be used in combination with another compound having two or more hydrazide groups or semicarbazide groups. Examples of the compound include a saturated aliphatic carboxylic acid dihydrazide having 2 to 18 carbon atoms such as oxalic acid dihydrazide, malonic acid dihydrazide, glutaric acid dihydrazide, succinic acid dihydrazide, adipic acid dihydrazide, and sebacic acid dihydrazide; a monoolefinic unsaturated dicarboxylic acid dihydrazide such as maleic acid dihydrazide, fumaric acid dihydrazide, and itaconic acid dihydrazide; an acid dihydrazide compound such as phthalic acid dihydrazide, terephthalic acid dihydrazide, isophthalic acid dihydrazide, pyromellitic acid dihydrazide, pyromellitic acid trihydrazide, and pyromellitic acid tetrahydrazide; nitrilotrihydrazide, citric acid trihydrazide, 1,2,4-benzene trihydrazide, ethylenediamine tetraacetic acid tetrahydrazide, 1,4,5,8-naphthoic acid tetrahydrazide, polyhydrazide produced by reacting a low polymer having a carboxylic acid lower alkyl ester group with hydrazine or a hydrazine hydrate (refer to Japanese Patent Publication No. 52-22878); carbonate dihydrazide and bis semicarbazide; polyfunctional semicarbazide obtained by reacting a polyisocyanate compound having an allophanate group obtained by allophanatization reaction after or in parallel with urethanization reaction between alcohols and diisocyanate such as hexamethylene diisocyanate and isophorone diisocyanate with a hydrazine compound or the dihydrazide exemplified above, an aqueous polyfunctional semicarbazides obtained by reacting an isocyanate group in a reaction product between the polyisocyanate compound and an active hydrogen compound containing a hydrophilic group of polyether polyols and polyethylene glycol monoalkyl ethers with the exemplified dihydrazide, or a mixture of the polyfunctional semicarbazide and an aqueous polyfunctional semicarbazide (refer to Japanese Patent Application Laid-Open No, Hei-8-151358, Japanese Patent Application Laid-Open No. Hei 8-245878, and Japanese Patent No. 3212857). Among them, the combination use with adipic acid dihydrazide having water-solubility is particularly preferred. The molar ratio between the semicarbazide composition and a compound for combination use is preferably in the range of 100/0 to 0.1/99.9, more preferably in the range of 90/10 to 10/90. With the combination use of the semicarbazide composition and another compound in coating film formation of an aqueous polymer composition, an excellent coating film having both of rigidity and flexibility, or having flexibility, stain resistance, hardness, etc., all together can be obtained.

The semicarbazide composition may be added to an aqueous polymer composition, for example, in an aqueous solution form diluted with water. Examples of the aqueous solutions include an aqueous solution containing 5 mass % or more (preferably 25 mass % or more, more preferably 40 mass % or more) of the semicarbazide composition. The semicarbazide composition concentration may be 95 mass % or less, preferably 80 mass % or less. Alternatively, the semicarbazide composition in a solid form may be directly added to an aqueous polymer composition without dilution with water or the like.

(Aqueous Polymer Composition)

The aqueous polymer composition of the present embodiment contains the semicarbazide composition described above and a polymer which can form a cross-linked structure by reacting with semicarbazide groups (hereinafter referred to as "polymer (E)"). According to the aqueous polymer composition of the present embodiment, a coating film having excellent hardness, stain resistance and alkali yellowing resistance can be formed, so that the aqueous polymer composition can be suitably used as a waterborne paint or a waterborne coating material.

The polymer (E) is not particularly limited as long as a cross-linked structure can be formed with a reaction with semicarbazide groups, and examples of the polymer (E) include a compound having a plurality of carbonyl groups (hereinafter referred to as "polycarbonyl compounds", a compound having a plurality of epoxy groups (hereinafter referred to as "polyepoxy compound"), and the like.

The polymer (E) is preferably obtained as a waterborne polymer dispersion by emulsion polymerization or the like. The waterborne polymer dispersion is a liquid composition with the polymer (E) dispersed in water, and a suitable aqueous polymer composition can be obtained by adding the semicarbazide composition to the waterborne polymer dispersion.

Among the polymers (E), a polycarbonyl compound is particularly preferred, because when combined with a semicarbazide composition, excellent storage stability of an aqueous polymer composition can be achieved and a coating film excellent in weather resistance, water resistance, stain resistance, hardness, etc. can be produced at relatively low temperature.

Examples of the polycarbonyl compound include a carbonyl group-containing copolymer, carbonyl group-containing polyurethanes made from raw material mono- or poly-alcohol having a carbonyl group such as hydroxyacetone described in Japanese Patent Application Laid-Open No. Hei-2-238015, acetoacetylated polyvinyl alcohol, a polyvinyl alcohol polymer having a di acetone group in a side chain described in Japanese Patent Application Laid-Open No. Hei-9-324095, acetoacetylated hydroxyalkyl cellulose, and a combination thereof.

Among these polycarbonyl compounds, a carbonyl group-containing copolymer produced by copolymerization of a carbonyl group-containing ethylenically unsaturated monomer (α) and an ethylenically unsaturated monomer (β) copolymerizable with the carbonyl group-containing ethylenically unsaturated monomer (α) is preferred, and a carbonyl group-containing copolymer produced by copolymerization of 0.1 to 30 mass % of a carbonyl group-containing ethylenically unsaturated monomer (α) and 70 to 99.9 mass % of an ethylenically unsaturated monomer (β) copolymerizable with the carbonyl group-containing ethylenically unsaturated monomer (α) is more preferred.

Examples of the carbonyl group-containing ethylenically unsaturated monomer (α) include diacetone acrylamide, diacetone methacrylamide, acrolein, vinyl methyl ketone, acetoacetoxyethyl methacrylate, acetoacetoxyethyl acrylate, and formylstyrol, and a combination thereof.

Examples of the ethylenically unsaturated monomer (β) copolymerizable with the carbonyl group-containing ethylenically unsaturated monomer (α) include an acrylic acid ester, a methacrylic acid ester, ethylenically unsaturated monomers having a carboxyl group, ethylenically unsaturated monomers having an epoxy group, an acrylamide monomer, a methacrylamide monomer, and vinyl cyanides; and examples of the (meth)acrylic acid ester include a (meth)acrylic acid alkyl ester with an alkyl portion having 1 to 18 carbon atoms, a (meth)acrylic acid hydroxyalkyl ester with an alkyl portion having 1 to 18 carbon atoms, a (poly)oxy-ethylene(meth)acrylate having 1 to 100 ethylene oxide groups, a (poly)oxypropylene(meth)acrylate having 1 to 100 propylene oxide groups, and (poly)oxyethylene di(meth)acrylate having 1 to 100 ethylene oxide groups.

Specific examples of the acrylic acid ester and the methacrylic acid ester include methyl(meth)acrylate, ethyl(meth)acrylate, n-butyl(meth)acrylate, iso-butyl(meth)acrylate tert-butyl(meth)acrylate, 2-ethylhexyl(meth)acrylate, methyl cyclohexyl(meth)acrylate, cyclohexyl(meth)acrylate, dodecyl(meth)acrylate, stearyl(meth)acrylate, and adamantyl(meth)acrylate.

Specific examples of the (meth)acrylic acid hydroxyalkyl ester include 2-hydroxyethyl(meth)acrylate, 2-hydroxypropyl(meth)acrylate, 2-hydroxycyclohexyl(meth)acrylate, and dodecyl(meth)acrylate.

Specific examples of the (poly)oxyethylene(meth)acrylate include ethylene glycol(meth)acrylate, ethylene glycol methoxy(meth)acrylate, diethylene glycol(meth)acrylate, diethylene glycol methoxy(meth)acrylate, tetraethylene glycol(meth)acrylate, and tetraethylene glycol methoxy(meth)acrylate.

Specific examples of the (poly)oxypropylene(meth)acrylate include propylene glycol(meth)acrylate, propylene glycol methoxy(meth)acrylate, dipropylene glycol(meth)acrylate, dipropylene glycol methoxy(meth)acrylate, tetrapropylene glycol(meth)acrylate, and tetrapropylene glycol methoxy(meth)acrylate.

Specific examples of the (poly)oxyethylene di(meth)acrylate include ethylene glycol di(meth)acrylate, diethylene glycol di(meth)acrylate, diethylene glycol methoxy(meth)acrylate, and tetraethylene glycol di(meth)acrylate.

Specific examples of the ethylenically unsaturated monomers having a carboxyl group include acrylic acid, methacrylic acid, itaconic acid, fumaric acid, maleic acid, a half ester of maleic acid, and crotonic acid.

Examples of the (meth)acrylamide monomers include (meth)acrylamide, N-isobutyl(meth)acrylamide, N-diethyl (meth)acrylamide, N-methylol(meth)acrylamide, N-butoxymethyl(meth)acrylamide, and vinyl pyrrolidone; examples of the vinyl cyanide include (meth)acrylonitrile; and examples of the ethylenically unsaturated monomers having an epoxy group include glycidyl(meth)acrylate, 2,3-cyclohexene oxide(meth)acrylate, and allyl glycidyl ether.

Specific examples other than the above include: olefins such as ethylene, propylene, and isobutylene; dienes such as butadiene; halo-olefins such as vinyl chloride and vinylidene chloride; carboxylic acid vinyl esters such as vinyl acetate, vinyl propionate, vinyl n-butyrate, vinyl benzoate, p-t-butyl vinyl benzoate, vinyl pivalate, vinyl 2-ethyl hexanoate, vinyl versatate, and vinyl laurate; carboxylic acid isopropenyl esters such as isopropenyl acetate and isopropenyl propionate; vinyl ethers such as ethyl vinyl ether, isobutyl vinyl ether and cyclohexyl vinyl ether; aromatic vinyl compounds such as styrene and vinyl toluene; allyl esters such as allyl acetate and allyl benzoate; allyl ethers such as allyl ethyl ether and allyl phenyl ether; γ-(meth)acryloxy propyltrimethoxysilane, 4-(meth)acryloyloxy-2,2,6,6-tetramethylpiperidine, 4-(meth)acryloyloxy-1,2,2,6,6-pentamethylpiperidine, perfluoromethyl(meth)acrylate, perfluoropropyl (meth)acrylate, perfluoropropylomethyl(meth)acrylate, vinylpyrrolidone, trimethylolpropane tri(meth)acrylate, and allyl(meth)acrylate, and combinations thereof.

The polycarbonyl compound is preferably obtained by suspension polymerization, emulsion polymerization, or solution polymerization, and more preferably obtained from a carbonyl group-containing waterborne polymer dispersion (aqueous polymer emulsion) by emulsion polymerization. A particularly suitable aqueous polymer composition can be obtained by preparing a polycarbonyl compound in a waterborne polymer dispersion form and adding a semicarbazide composition to the waterborne polymer dispersion.

The waterborne polymer dispersion is preferably a carbonyl group-containing acrylic copolymer dispersion with use of acrylic monomers. Preferably the polycarbonyl compound is obtained as waterborne polymer dispersion by copolymerizing a carbonyl group-containing ethylenically unsaturated monomer (α) and an ethylenically unsaturated monomer (β) under presence of an anion-type ethylenically unsaturated monomer (γ) selected from the group consisting of, for example, an ethylenically unsaturated monomer having a sulfonic acid group or a sulfonate group, an ethylenically unsaturated monomer having a sulfonic acid ester group, and a mixture thereof.

Emulsion polymerization to produce the polymer (E) (polycarbonyl compound, in particular) can be performed in an aqueous medium using a surfactant. As the surfactant for use in the emulsion polymerization, a so-called reactive surfactant having an ethylenic double bond group in the chemical structural formula of the surfactant having a hydrophilic group and a lipophilic group, so as to impart high water resistance to a coating film.

Among the reactive surfactants, examples of the anionic surfactant include an ethylenically unsaturated monomer having a sulfonic acid group, a sulfonate group, a sulfonic acid ester group, or a salt thereof; and a compound having a sulfonic acid group, an ammonium salt of sulfonic acid group (ammonium sulfonate group), or a group as alkali metal salt of sulfonic acid group (alkali metal sulfonate group) can be suitably used. Specific examples include alkyl allyl sulfosuccinate (e.g. trade name: ELEMINOL JS-2 and JS-5, made by Sanyo Chemical Industries, Ltd.; and trade name: LAIEMUL S-120, S-180A, and S-180, made by Kao Corporation), polyoxyethylene alkyl propenyl phenyl ether sulfate (e.g. trade name: Aqualon HS-10, made by Dai-ichi Kogyo Seiyaku Co., Ltd.), α-[1-[(allyloxy)methyl]-2-(phenylphenoxy)ethyl]-ω-polyoxyethylene sulfate (e.g trade name: ADEKARIA SOAP SE-1025A, made by Adeka Corporation), an ammonium salt of α-sulfo-ω-(1-(alkoxy)

methyl)-2-(2-propenyloxy)ethoxy)-poly(oxy-1-2-ethanediyl) (e.g. trade name: SR-1025, made by Adeka Corporation), and ammonium=α-sulfonate-ω-1-(allyloxymethyl)alkyloxy polyoxyethylene (e.g. trade name: AQUALON KH-10, made by Dai-ichi Kogyo Seiyaku Co., Ltd.). Specific examples of the compound having aryl groups partially substituted with sulfonate groups include an ammonium salt, a sodium salt, and a potassium salt of p-styrene sulfonic acid. Examples of the vinyl sulfonate compound having a vinyl group to which the group of ammonium salt, sodium salt, or potassium salt of a sulfonic acid group is bonded include alkyl sulfonic acid (meth)acrylate such as 2-sulfoethyl acrylate, and an ammonium salt, sodium salt, and potassium salt of methyl propane sulfonic acid (meth) acrylamide, allyl sulfonic acid, etc.

Examples of the nonionic surfactant include α-[1-[(allyloxy)methyl]-2-(phenylphenoxy)ethyl]-ω-hydroxy-polyoxyethylene (e.g. trade name: ADEKARIA SOAP NE-20, NE-30, NE-40, ER-10, ER-20, ER-30, and ER-40, made by Adeka Corporation), and polyoxyethylene alkyl propenylphenyl ether (e.g. trade name: AQUALON RN-10, RN-20, RN-30, and RN-50, made by Dai-ichi Kogyo Seiyaku Co., Ltd.).

In emulsion polymerization, a conventional surfactant may be used other than the reactive surfactant having an ethylenic double bond group in the chemical structural formula of the surfactant having a hydrophilic group and a lipophilic group. Examples of such a surfactant include an anion-type surfactant such as a fatty acid soap, alkyl sulfonate, alkylbenzene sulfonate, alkyl sulfosuccinate, polyoxyethylene alkyl sulfate, and polyoxyethylene alkyl aryl sulfate; and a nonreactive nonionic surfactant such as polyoxyethylene alkyl ether, polyoxyethylene alkyl aryl ether, polyoxyethylene sorbitan fatty acid ester, and an oxyethylene oxypropylene block copolymer.

Each of the surfactants may be used alone, or two or more thereof may be used in combination, and the amount thereof used may be typically 0.05 mass % to 10 mass %, preferably 0.1 mass % to 5 mass % relative to the total mass of the radical polymerizable monomers to produce the polymer (E). With an amount of the surfactant used of 0.05 mass % or more, the polymerization stability is high with less occurrence of aggregates in emulsion polymerization; and with an amount used of 10 mass % or less, the water resistance of a coating film obtained from the aqueous polymer composition including the polymer (E) produced by emulsion polymerization can be further improved. A reactive surfactant is preferred from the viewpoint of further improvement in water resistance and weather resistance of a coating film.

In emulsion polymerization, a compound able to cause addition polymerization of radically polymerizable unsaturated monomers by radical decomposition with heating or reducing material can be used as radical polymerization initiator.

As the radical polymerization initiator, a water-soluble or oil-soluble persulfate salt, peroxide, an azobis compound and the like can be used. Examples thereof include potassium persulfate, sodium persulfate, ammonium persulfate, hydrogen peroxide, t-butyl hydroperoxide, t-butyl peroxybenzoate, 2,2-azobis(isobutyronitrile), 2,2-azobis(2-diaminopropane)hydrochloride, and 2,2-azobis(2,4-dimethylvaleronitrile); and the amount used can be 0.1 to 1 mass % relative to the ethylenically unsaturated monomer.

Although the emulsion polymerization is preferably performed typically at a polymerization temperature of 65 to 90° C. under normal pressure, it may be also performed under high pressure corresponding to the properties of the monomer such as vapor pressure at the polymerization temperature. When acceleration of the polymerization rate or polymerization at a low temperature of 70° C. or lower is desired, use of a reducing agent such as sodium bisulfite, ferrous chloride, ascorbate, and Rongalite, in combination with a radical polymerization initiator is advantageous. Further, a chain transfer agent such as dodecyl mercaptan may be optionally added for regulation of the molecular weight.

Since the aqueous polymer composition containing a polycarbonyl compound as the polymer (E) has long-term storage stability, preferably the pH is adjusted to within the range of 5 to 10. For the pH adjustment, ammonia, sodium hydroxide, potassium hydroxide, amines such as dimethyl amino ethanol, acids such as hydrochloric acid, sulfuric acid, acetic acid, and lactic acid may be added to the aqueous polymer composition.

Examples of the polyepoxy compound as the polymer (E) include an epoxy group-containing copolymer produced by copolymerization of epoxy group-containing ethylenically unsaturated monomers such as glycidyl(meth)acrylate with other unsaturated monomers by bulk polymerization, suspension polymerization, emulsion polymerization, solution polymerization, or the like; a bisphenol A-type epoxy resin; a bisphenol F-type epoxy resin; an alicyclic epoxy resin; a glycidyl ester type epoxy resin; a glycidyl amine epoxy resin; a hydantoin epoxy resin; and triglycidylisocyanurate; which may be used in combination. Preferably these polyepoxy compounds are dispersed in water for use in a waterborne polymer dispersion form.

Examples of the waterborne polymer dispersion of a polyepoxy compound dispersed in water include an epoxy group-containing acrylic copolymer aqueous dispersion. The epoxy group-containing acrylic copolymer aqueous dispersion can be produced, for example, by the same way as in the production of the carbonyl group-containing waterborne polymer dispersion except for the type of monomers for use. As the epoxy group-containing ethylenically unsaturated monomer, glycidyl(meth)acrylate can be suitably used.

As the polymer (E), a polyepoxy compound having a part of or the entire of epoxy groups ring-opened with addition of water can be used. Such a compound can be obtained by heating a polyepoxy compound-containing waterborne polymer dispersion or an aqueous polymer composition.

The aqueous polymer composition has a mass ratio of the semicarbazide composition content $C_1$ to the polymer (E) content $C_2$, i.e. $C_1/C_2$, in the range of preferably 0.1/99.9 to 90/10. Within the range, the aqueous polymer composition can have both cold curing ability and storage stability, and a coating film produced from the aqueous polymer composition is excellent in water resistance, stain resistance, hardness, etc. With a ratio $C_1/C_2$ of less than 0.1/99.9, the effect of cross-linking cannot be achieved due to lowered cross-linking density, which is undesirable. With a ratio $C_1/C_2$ of more than 90/10, the coating film to be produced is extremely brittle, which is undesirable.

The aqueous polymer composition can be suitably used as a waterborne paint or a waterborne coating material. A component other than the semicarbazide composition and the polymer (E) may be added to the aqueous polymer composition, corresponding to the application.

The aqueous polymer composition may contain, for example, a known ultraviolet absorber such as benzophenone, benzotriazole, or triazin, and a known photostabilizer such as hindered phenol or hindered amine. Further, components commonly added to a waterborne paint or the like, such as a pigment, a filler, a dispersant, a wetting agent, a thickener, a rheology control agent, a defoamer, a plasticizer, a coalescing agent, a rust inhibitor, a dye, and a preservative, can be selected and formulated in combination so as to be added to the aqueous polymer composition on an as needed basis.

[Description of a Preferred Aspect of the Aqueous Polymer Composition]

One preferred aspect of the aqueous polymer composition of the present embodiment is described in the following. The aqueous polymer composition in the present aspect is an aqueous polymer composition including a cross-linking agent and a waterborne polymer dispersion which are blended. In the present aspect, the cross-linking agent contains the semicarbazide composition described above. The waterborne polymer dispersion includes at least one cross-linkable polymer having a glass transition temperature Tg of lower than 80° C., selected from the group consisting of a water-soluble or water-dispersible polycarbonyl compound having a number average molecular weight of 1000 to 100000, and a water-soluble or water-dispersible polyepoxy compound having a number average molecular weight of 1000 to 100000.

<Cross-Linking Agent>

The cross-linking agent contains the semicarbazide composition described above. The semicarbazide composition is nonreactive with an aldo group, a keto group, an epoxy group, etc., of a cross-linkable polymer in the presence of water in the aqueous polymer composition, and reactive with these groups when water disappears, capable of being suitably used as a cross-linking agent for a one-pack type waterborne paint or a waterborne coating material.

The semicarbazide composition can be used as a cross-linking agent, for example, in an aqueous solution form diluted with water. Examples of the aqueous solution include an aqueous solution containing the semicarbazide composition in an amount of 5 mass % or more (preferably 25 mass % or more, more preferably 40 mass % or more). The concentration of the semicarbazide composition in the aqueous solution may be 95 mass % or less, preferably 80 mass % or less. Alternatively, the solid semicarbazide composition can be directly used as a cross-linking agent without dilution with water or the like.

As the cross-linking agent, a cross-linking agent other than the semicarbazide composition may also be used in combination. As such a cross-linking agent, for example, a compound having two or more hydrazide groups or semicarbazide groups is suitable, and specific examples thereof include a saturated aliphatic carboxylic acid dihydrazide having 2 to 18 carbon atoms such as oxalic acid dihydrazide, malonic acid dihydrazide, glutaric acid dihydrazide, succinic acid dihydrazide, adipic acid dihydrazide and sebacic acid dihydrazide; mono-olefinic unsaturated dicarboxylic acid dihydrazide such as maleic acid dihydrazide, fumaric acid dihydrazide, itaconic acid dihydrazide; an acid dihydrazide compound such as phthalic acid dihydrazide, terephthalic acid dihydrazide, isophthalic acid dihydrazide, pyromellitic acid dihydrazide, pyromellitic acid trihydrazide, pyromellitic acid tetrahydrazide; nitrilotrihydrazide, citric acid trihydrazide, 1,2,4-benzene trihydrazide, ethylenediamine tetraacetic acid tetrahydrazide, 1,4,5,8-naphthoic acid tetrahydrazide, polyhydrazide produced by reacting a low polymer having carboxylic acid lower alkyl ester group with hydrazine or hydrazine hydrate (refer to Japanese Patent Publication No. 52-22878); carbonate dihydrazide and bis semicarbazide; polyfunctional semicarbazide obtained by reacting a polyisocyanate compound having an allophanate group obtained by allophanatization reaction after or in parallel with urethanization reaction between alcohols and diisocyanate such as hexamethylene diisocyanate and isophorone diisocyanate with a hydrazine compound or the dihydrazide exemplified above, an aqueous polyfunctional semicarbazide obtained by reacting an isocyanate group in a reaction product between the polyisocyanate compound and an active hydrogen compound containing a hydrophilic group of polyether polyols and polyethylene glycol monoalkyl ethers with the exemplified dihydrazide, or a mixture of the polyfunctional semicarbazide and an aqueous polyfunctional semicarbazide (refer to Japanese Patent Application Laid-Open No. Hei-8-151358, Japanese Patent Application Laid-Open No. Hei 8-245878, and Japanese Patent No. 3212857). Among them, the combination use with adipic acid dihydrazide having water-solubility is particularly preferred. The molar ratio between the semicarbazide composition and a compound for combination use is preferably in the range of 100/0 to 0.1/99.9, more preferably in the range of 90/10 to 10/90. With the combination use of the semicarbazide composition and another compound in coating film formation of an aqueous polymer composition, an excellent coating film having both of rigidity and flexibility, or having flexibility, stain resistance, hardness, etc., all together can be obtained.

The amount of the cross-linking agent blended is controlled to have a ratio $M_1/M_2$, i.e. the total amount $M_1$ of semicarbazide groups and hydrazine groups in a cross-linking agent to the total amount $M_2$ of cross-linkable groups contained in the polymer component in an waterborne polymer dispersion, of preferably in the range of 0.01 to 10, more preferably in the range of 0.05 to 5, furthermore preferably in the range of 0.1 to 2.

<Waterborne Polymer Dispersion>

In the present aspect, the waterborne polymer dispersion is a liquid composition containing an aqueous dispersion medium and a polymer component dispersed in the aqueous dispersion medium, and the polymer component contains at least one cross-linkable polymer selected from the group consisting of a water-soluble or water-dispersible polycarbonyl compound having a number average molecular weight of 1000 to 100000, and a water-soluble or water-dispersible polyepoxy compound having a number average molecular weight of 1000 to 100000.

The term "water-soluble or water-dispersible" includes being dissolved in water or being dispersed in water to form an emulsion partially dissolved in water.

The aqueous dispersion medium contains at least water, and contains a water-soluble organic solvent in some cases. The water content in the aqueous dispersion medium is preferably 5 mass % or more, more preferably 50 mass % or more.

The polymer component content in a waterborne polymer dispersion is preferably 1 to 70 mass %, more preferably 5 to 67 mass %, relative to the total amount of the waterborne polymer dispersion.

(Water-Soluble or Water-Dispersible Polycarbonyl Compound)

The water-soluble or water-dispersible polycarbonyl compound (hereinafter referred to simply as "polycarbonyl compound") is a compound having at least two or more of aldo groups or keto groups. Examples of the polycarbonyl compound include a conventionally known polycarbonyl compound such as polyurethane, polyester, poly(meth)acrylate, polyvinyl acetate, polybutadiene, polyvinyl chloride, chlorinated polypropylene, polyethylene, polystyrene, a polystyrene-(meth)acrylate copolymer, a rosin derivative, a styrene-maleic anhydride copolymer and an alcohol adduct thereof, and a cellulose polymer, and one or a plurality of these may be used.

The polycarbonyl compound can be obtained by copolymerization or addition polymerization of a monomer having at least one aldo group or keto group in the molecule with other monomer. It is presumed that the aldo group and the keto group are involved in the cross-linking reaction as a carbonyl group after polymerization reaction.

Specific examples of the monomer having at least one aldo group or keto group in the molecule include acetone dicarboxylic acid, dihydroxyacetone, monohydroxyacetone, and dihydroxybenzaldehyde, and a polycarbonyl compound can be obtained by addition polymerization of a single one thereof or a plurality thereof in combination.

Specific examples of the ethylenically unsaturated monomer having at least one aldo group or keto group in the molecule include acrolein, diacetone acrylamide, diacetone methacrylamide, formylstyrol, vinyl methyl ketone, vinyl ethyl ketone, vinyl isobutyl ketone, acryloxyalkyl propanals, methacryloxyalkyl propanals, diacetone acrylate, diacetone methacrylate, acetonyl acrylate, 2-hydroxypropyl acrylate acetyl acetate, and butanedio-1,4-acrylate acetyl acetate, and a polycarbonyl compound can be obtained by polymerizing one or more thereof with an ethylenically unsaturated monomer mixture containing an ethylenically unsaturated monomer other than these. An ethylenically unsaturated monomer having a carbonyl group belonging to a carboxylic acid or an ester, however, is excluded from the ethylenically unsaturated monomer having at least one aldo group or keto group in the molecule.

Preferably the monomer mixture for obtaining the polycarbonyl compound includes 0.5 wt. % or more of an ethylenically unsaturated monomer having at least one aldo group or keto group in the molecule. With a content of the ethylenically unsaturated monomer having an aldo group or keto group in a monomer mixture of 0.5 wt. % or more, sufficient performance of a coating film can be achieved with increased cross-linking points. More preferably, the content is 0.5 wt. % or more and 20 wt. % or less.

The polycarbonyl compound may be any of anionic, cationic, nonionic, and amphoteric. Among them, being anionic is preferred, and being anionic due to inclusion of carboxylic acid groups is particularly preferred from the viewpoint of enhancing the solubility in water.

A polycarbonyl compound having a carboxylic acid group has an acid value. In order to allow a polycarbonyl compound to retain a carboxylic acid group, an ethylenically unsaturated carboxylic acid monomer is mixed with the monomer mixture for use in polymerization. Examples of the ethylenically unsaturated carboxylic acid monomer include acrylic acid, methacrylic acid, itaconic acid, fumaric acid, maleic acid, maleic anhydride, and a half-ester of itaconic acid, fumaric acid, or maleic acid.

The acid value of the polycarbonyl compound is preferably 20 mg KOH/g or more, more preferably 25 mg KOH/g or more, furthermore preferably 25 mg KOH/g or more and 350 mg KOH/g or less. With an acid value of 20 mg KOH/g or more, the polycarbonyl compound has increased solubility in water, so that the fusion between emulsion particles and the mutual diffusion of molecules can be facilitated. The acid value is expressed by the solid weight of KOH used for neutralization relative to the gram-weight of dry polymer.

The coating film obtained from the aqueous polymer composition hardly causes whitening of the coating film when immersed in water. Though a cause for whitening of the coating film when immersed in water is presumed to be intrusion of water into the fused part of emulsion particles, the fused part of emulsion particles of the present invention is hydrophobized by the cross-linking reaction of the semicarbazide composition. In the present embodiment, therefore, whitening of the coating film when immersed in water can be sufficiently suppressed even for the polycarbonyl compound having high solubility in water with an acid value of 20 mg KOH/g or more.

Examples of the nonionic polycarbonyl compound include the compound of a water-soluble polymer having a hydroxyl group and a derivative thereof such as cellulose, methyl cellulose (MC), carboxymethyl cellulose (CMC), polyvinyl alcohol (PVA), polyethylene glycol (PEG), or polypropylene glycol (PPG), which are modified with diketene, pyruvic acid, levulinic acid, acetoacetic acid, trimethyl pyruvate, propionyl acetate, benzoyl formate, phenylpyruvate, ketocapric acid, ketoundecanoic acid, ketostearic acid, ketoheneicosenoic acid, benzoyl acetate, benzoyl propionate, ketogluconic acid, ketomalonic acid, acetone dicarboxylic acid, 2-ketoglutaric acid, acetone diacetic acid, acetone propionic acid, or a derivative thereof. These compounds are produced typically by addition reaction in a solution or in a fused state under presence or absence of acid, alkali, etc., with adjustment of the amount of modification to the extent that the solubility in water can be maintained, while removing the hydroxyl compounds as by-product.

In the case of a cationic polycarbonyl compound, the monomer mixture for use in polymerization contains an ethylenically unsaturated monomer having a cationic group.

Examples of the ethylenically unsaturated monomer having a cationic group include dimethylaminoethyl(meth)acrylate and salt, diethylaminoethyl(meth)acrylate and salt, dimethylaminopropyl(meth)acrylate and salt, dimethylaminomethyl(meth)acrylamide and salt, dimethylaminoethyl(meth)acrylamide and salt, dimethylaminopropyl(meth)acrylamide and salt, vinyl pyridine, halide salt of dimethylamino methyl(meth)acrylamide epichlorohydrin adduct, halide salt and alkylsulfonate of dimethylaminopropyl(meth)acrylamide epichlorohydrin adduct, halide salt of dimethylaminomethyl(meth)acrylate epichlorohydrin adduct, halide salt and alkylsulfonate of dimethylaminopropyl(meth)acrylate epichlorohydrin adduct.

The amount of the ethylenically unsaturated monomer having a cationic group for use in a monomer mixture is preferably 0.5 wt. % to 30 wt. %, more preferably 1 wt. % to 20 wt. %. The polycarbonyl compound having better solubility in water can be thus obtained.

The polycarbonyl compound has a number average molecular weight of 1000 to 100000, preferably 1000 to 50000, more preferably 4000 to 50000. It is presumed that due to having a water-soluble component with a relatively low molecular weight, the aqueous polymer composition can be handled as an aqueous dispersion or an aqueous solution with low viscosity, so that a coating film can be easily formed by fusion of emulsion particles, and the cross-linking reaction with a semicarbazide composition can be rapidly caused.

(Water-Soluble or Water-Dispersible Polyepoxy Compound)

A water-soluble or water-dispersible polyepoxy compound (hereinafter referred to simply as "polyepoxy compound") is a compound having two or more epoxy groups or ring-opened epoxy group.

The ring-opened epoxy group is a group produced by ring-opening reaction of an epoxy group, which can be represented by —X—C—C(—OH)—. In the formula, X represents an oxygen atom or a nitrogen atom. Examples of the ring-opened epoxy group include a ring-opened glycidyl group. The ring-opened glycidyl group is a group produced by ring-opening reaction of a glycidyl group, which can be represented by —X—CH$_2$—C(—OH)—CH$_2$—. Examples of the ring-opening reaction include the reaction between an epoxy group and a carboxyl group, and a reaction between an epoxy group and an amino group.

The polyepoxy compound can be obtained by changing an ethylenically unsaturated monomer having at least one aldo group or keto group in the molecule into an ethylenically unsaturated monomer having at least one epoxy group in the molecule, in the production process of the polycarbonyl compound. More specifically, the polyepoxy compound can be obtained by copolymerizing an ethylenically unsaturated monomer having at least one epoxy group in the molecule with other monomer.

Further, the polyepoxy compound having two or more ring-opened epoxy groups may be obtained, for example, by reacting a compound having two or more carboxyl groups or amino groups with two or more equivalents of a compound having at least one epoxy groups under presence of a catalyst. Alternatively the polyepoxy compound having two or more ring-opened epoxy groups may be obtained by reacting a compound having two or more epoxy groups with two or more equivalents of a compound having at least one carboxyl group or amino groups under presence of a catalyst. On this occasion, a catalyst for use as curing catalyst such as a tertiary amine and a quaternary ammonium salt can be used as the catalyst; more specifically, tetra-n-butyl ammonium hydroxide, methyltributyl ammonium hydroxide, benzyltriethyl ammonium hydroxide, and the like can be used.

Examples of the ethylenically unsaturated monomer having one or more epoxy groups include glycidyl(meth)acrylate, allyl glycidyl ether, glycidyl cinnamate, glycidyl crotonate, glycidyl itaconate, glycidyl, glycidyl norbornenyl ester, and glycidyl norbornenyl ether.

A compound having an epoxy group can be used as the compound having at least one epoxy group in the molecule for producing a polyepoxy compound having a ring-opened epoxy group without specific limitations, and specific examples thereof include a reaction product of a compound having at least one carboxyl group and epichlorohydrin, and the like.

The polyepoxy compound has a number average molecular weight of, preferably 1000 to 100000, more preferably 1000 to 50000, furthermore preferably 4000 to 50000.

The polyepoxy compound may be any of anionic, cationic, nonionic, and amphoteric. Among them, being anionic is preferred, and being anionic due to inclusion of a carboxylic acid group is particularly preferred from the viewpoint of enhancing the solubility in water.

A polyepoxy compound having a carboxylic acid group has an acid value. In order to allow a polyepoxy compound to retain a carboxylic acid group, an ethylenically unsaturated carboxylic acid monomer is mixed with the monomer mixture for use in polymerization. Examples of the ethylenically unsaturated carboxylic acid monomer include acrylic acid, methacrylic acid, itaconic acid, fumaric acid, maleic acid, maleic anhydride, and a half ester of itaconic acid, fumaric acid, or maleic acid.

The acid value of the polyepoxy compound is preferably 20 mg KOH/g or more, more preferably 25 mg KOH/g or more, furthermore preferably 25 mg KOH/g or more and 350 mg KOH/g or less. With an acid value of 20 mg KOH/g or more, the polyepoxy compound has increased solubility in water, so that the fusion between emulsion particles and the mutual diffusion of molecules can be facilitated. The acid value is expressed by the solid weight of KOH used for neutralization relative to the gram-weight of dry polymer.

The coating film obtained from the aqueous polymer composition hardly causes whitening of the coating film when immersed in water. Though a cause for whitening of the coating film when immersed in water is presumed to be intrusion of water into the fused part of emulsion particles, the fused part of emulsion particles of the present invention is hydrophobized by the cross-linking reaction of the semicarbazide composition. In the present aspect, therefore, whitening of the coating film when immersed in water can be sufficiently suppressed even for the polyepoxy compound having high solubility in water with an acid value of 20 mg KOH/g or more.

As described above, a monomer having at least one aldo group or keto group in the molecule or a monomer having at least one epoxy group and other monomer component can be copolymerized to produce a polycarbonyl compound or a polyepoxy compound, and examples of the other monomer component for use include acrylic acid ester, methacrylic acid ester, an acrylamide monomer, a methacrylamide monomer, and vinyl cyanides.

Examples of the (meth)acrylic acid ester include a (meth)acrylic acid alkyl ester with an alkyl portion having 1 to 18 carbon atoms, a (meth)acrylic acid hydroxyalkyl ester with an alkyl portion having 1 to 18 carbon atoms, a (poly)oxyethylene(meth)acrylate having 1 to 100 ethylene oxide groups, a (poly)oxypropylene(meth)acrylate having 1 to 100 propylene oxide groups, and (poly)oxyethylene di(meth)acrylate having 1 to 100 ethylene oxide groups.

Specific examples of the methacrylic acid esters include methyl(meth)acrylate, ethyl(meth)acrylate, n-butyl(meth)acrylate, iso-butyl(meth)acrylate tert-butyl(meth)acrylate, 2-ethylhexyl(meth)acrylate, cyclohexyl(meth)acrylate, methylcyclohexyl(meth)acrylate, dodecyl(meth)acrylate, isobornyl(meth)acrylate, stearyl(meth)acrylate, and adamantyl(meth)acrylate.

Specific examples of the (meth)acrylic acid hydroxyalkyl ester include 2-hydroxyethyl(meth)acrylate, 2-hydroxypropyl(meth)acrylate, 2-hydroxycyclohexyl(meth)acrylate, and dodecyl(meth)acrylate.

Specific examples of the (poly)oxyethylene(meth)acrylate include ethylene glycol(meth)acrylate, ethylene glycol methoxy(meth)acrylate, diethylene glycol(meth)acrylate, diethylene glycol methoxy(meth)acrylate, tetraethylene glycol(meth)acrylate, and tetraethylene glycol methoxy(meth)acrylate.

Specific examples of the (poly)oxypropylene(meth)acrylate include propylene glycol(meth)acrylate, propylene glycol methoxy(meth)acrylate, dipropylene glycol(meth)acrylate, dipropylene glycol methoxy(meth)acrylate, tetrapropylene glycol(meth)acrylate, and tetrapropylene glycol methoxy(meth)acrylate.

Specific examples of the (poly)oxyethylene di(meth)acrylate include ethylene glycol di(meth)acrylate, diethylene glycol di(meth)acrylate, diethylene glycol methoxy(meth)acrylate, and tetraethylene glycol di(meth)acrylate.

Examples of the (meth)acrylamide monomers include (meth)acrylamide, N-isobutyl(meth)acrylamide, N-dimethyl(meth)acrylamide, N-diethyl(meth)acrylamide, N-methylol(meth)acrylamide, and N-butoxymethyl(meth)acrylamide, and examples of the vinyl cyanides include (meth)acrylonitrile.

Specific examples other than the above include: olefins such as ethylene, propylene, and isobutylene; dienes such as butadiene; halo-olefins such as vinyl chloride and vinylidene chloride; carboxylic acid vinyl esters such as vinyl acetate, vinyl propionate, vinyl n-butyrate, vinyl benzoate, p-t-butyl vinyl benzoate, vinyl pivalate, vinyl 2-ethyl hexanoate, vinyl versatate, and vinyl laurate; carboxylic acid isopropenyl esters such as isopropenyl acetate and isopropenyl propionate; vinyl ethers such as ethyl vinyl ether, isobutyl vinyl ether and cyclohexyl vinyl ether; aromatic vinyl compounds such as styrene and vinyl toluene; allyl esters such as allyl acetate and allyl benzoate; allyl ethers such as allyl ethyl ether, allyl glycidyl ether, and allyl phenyl ether; γ-(meth) acryloxy propyltrimethoxysilane, vinyl methyl diethoxysilane, vinyl methyl dimethoxysilane, vinyl dimethyl ethoxysilane, vinyl dimethyl methoxysilane, vinyl trimethoxysilane, vinyl triethoxysilane, 4-(meth)acryloyloxy-2,2,6,6-tetramethylpiperidine, 4-(meth)acryloyloxy-1,2,2,6,6-pentamethylpiperidine, perfluoromethyl(meth)acrylate, perfluoropropyl(meth)acrylate, perfluoropropylomethyl(meth)acrylate, vinylpyrrolidone, trimethylolpropane tri(meth)acrylate, 2,3-cyclohexene oxide(meth)acrylate, allyl(meth)acrylate, acid phosphoxyethyl methacrylate, 3-chloro-2-acid phosphoxypropyl methacrylate, methylpropane sulfonic acid acrylamide, and divinylbenzene, and combinations thereof.

The cross-linkable polymer has a glass transition temperature Tg of lower than 80° C., preferably 65° C. or lower, more preferably 50° C. or lower. With a glass transition temperature of 80° C. or higher, the aqueous polymer composition tends to have poor coating film formation properties.

The Tg of the cross-linkable polymer may be calculated by applying the following Fox equation to the monomers constituting the polymer.

$$1/Tg = a_1/Tg_1 + a_2/Tg_2 + \ldots + a_n/Tg_n;$$ Fox equation:

wherein $a_1, a_2, \ldots a_n$ represent the mass fractions of the respective monomers, and $Tg_1, Tg_2, \ldots Tg_n$ represent Tg of homopolymers of the respective monomers. The Tg of the homopolymer of each monomer for use in calculation is described, for example, in Polymer Handbook (John Wiley & Sons), Introduction to Synthetic Polymer for Paint.

The cross-linkable polymer is obtained preferably by emulsion polymerization, mini-emulsion polymerization or solution polymerization.

The solution polymerization may be performed by a conventional method, and examples of the organic solvent for use include toluene, xylene, cyclohexane, ethyl acetate, butyl acetate, CS-12 (made by JNC Corporation), ethylene glycol monobutyl ether, ethylene glycol mono-2-ethylhexyl ether, ethylene glycol monoethyl ether, ethylene glycol monobutyl ether acetate, ethylene glycol mono-2-ethylhexyl ether acetate, ethylene glycol monoethyl ether acetate, diethylene glycol monobutyl ether, diethylene glycol monobutyl ether acetate, propylene glycol monoethyl ether, propylene glycol monopropyl ether, propylene glycol monobutyl ether, dipropylene glycol monoethyl ether, dipropylene glycol monopropyl ether, dipropylene glycol monobutyl ether, benzyl alcohol, dimethyl glutarate, and isopropyl glutarate.

Emulsion polymerization and mini-emulsion polymerization can be performed using a surfactant, and an anionic surfactant or a nonionic surfactant is used as the surfactant in production of an anionic cross-linkable polymer.

A reactive surfactant having an ethylenic double bond group in the chemical structural formula of the surfactant having a hydrophilic group and a lipophilic group may be used as the surfactant so as to impart high water resistance to a coating film.

Among the reactive surfactants, examples of the anionic surfactant include an ethylenically unsaturated monomer having a sulfonic acid group, a sulfonate group, a sulfonic acid ester group, or a salt thereof; and a compound having a sulfonic acid group, an ammonium salt of sulfonic acid group (ammonium sulfonate group), or a group as alkali metal salt of sulfonic acid group (alkali metal sulfonate group) can be suitably used.

Specific examples include allyl sulfonic acid, p-styrene sulfonic acid, alkyl allyl sulfosuccinate (e.g. trade name: ELEMINOL JS-2 and JS-5, made by Sanyo Chemical Industries, Ltd.; and trade name: LATEMUL S-120, S-180A, and S-180, made by Kao Corporation), polyoxyethylene alkyl propenyl phenyl ether sulfate (e.g. trade name: Aqualon HS-10, made by Dai-ichi Kogyo Seiyaku Co., Ltd.), α-[1-[(allyloxy)methyl]-2-(phenylphenoxy)ethyl]-ω-polyoxyethylene sulfate (e.g. trade name: ADEKARIA SOAP SE-1025A, made by Adeka Corporation), an ammonium salt of α-sulfo-ω-(1-(alkoxy)methyl)-2-(2-propenyloxy)ethoxy)-poly(oxy-1-2-ethanediyl) (e.g. trade name: SR-1025, made by Adeka Corporation), and ammonium=α-sulfonate-ω-1-(allyloxymethyl)alkyloxy polyoxyethylene (e.g. trade name: AQUALON KH-10, made by Dai-ichi Kogyo Seiyaku Co., Ltd.).

Among the reactive surfactants, examples of the nonionic surfactant include α-[1-[(allyloxy)methyl]-2-(phenylphenoxy)ethyl]-ω-hydroxy-polyoxyethylene (e.g. trade name: ADEKARIA SOAP NE-20, NE-30, and NE-40, made by Adeka Corporation), and polyoxyethylene alkyl propenyl-phenyl ether (e.g. trade name: AQUALON RN-10, RN-20, RN-30, and RN-50, made by Dai-ichi Kogyo Seiyaku Co., Ltd.).

In emulsion polymerization or mini-emulsion polymerization for producing the cross-linkable polymer in the present aspect, a conventional surfactant may be used other than the reactive surfactant having an ethylenic double bond group in the chemical structural formula of the surfactant having a hydrophilic group and a lipophilic group. Examples of such a surfactant include an anion-type surfactant such as a fatty acid soap, alkyl sulfonate, alkylbenzene sulfonate, alkyl sulfosuccinate, polyoxyethylene alkyl sulfate, and polyoxyethylene alkyl aryl sulfate; and a nonreactive nonionic surfactant such as polyoxyethylene alkyl ether, polyoxyethylene alkyl aryl ether, polyoxyethylene sorbitan fatty acid ester, and an oxyethylene oxypropylene block copolymer.

The amount of the surfactant for use is preferably 0.05 to 20 wt. % relative to the total mass of the monomers for producing a cross-linkable polymer. The surfactant may contain a plurality of surfactants for use in combination, and emulsion polymerization can be performed according to the conventional conditions without specific limitations.

In the polymerization reaction for producing the cross-linkable polymer, a radical polymerization initiator can be used. A compound to cause radical polymerization of ethylenically unsaturated monomers by radical decomposition with heating or reducing material can be used as radical polymerization initiator.

Among the radical polymerization initiators, a water-soluble persulfate salt, a peroxide, an azobis compound and the like can be used as the water-soluble initiator, and examples thereof include potassium persulfate, sodium persulfate, ammonium persulfate, hydrogen peroxide, t-butyl hydroperoxide, and 2,2-azobis(2-diaminopropane)hydrochloride. Among the radical polymerization initiators, examples of the oil-soluble initiator include t-butyl peroxybenzoate, 2,2-azobis(isobutyronitrile), and 2,2-azobis(2,4- dimethylvaleronitrile). When the polymerization reaction for producing the cross-linkable polymer is performed by emulsion polymerization, use of a water-soluble initiator is preferred, while when performed by solution polymerization or mini-emulsion polymerization, use of an oil-soluble initiator is preferred.

The radical polymerization initiator is blended typically in an amount of 0.1 to 10 mass % relative to the total of the entire monomers. When acceleration of the polymerization rate or the polymerization at low temperature is desired, a reducing agent such as sodium bisulfite, ferrous chloride, ascorbate, and Rongalite, may be used in combination with a radical polymerization initiator.

In the case of a monomer having an anion group for producing the cross-linkable polymer, an alkali may be added to the reaction system for neutralization or solubilization of the anion group in polymerization with a water-soluble polymerization initiator; while in the case of a monomer having a cation group for producing the cross-linkable polymer, an acid may be added to the reaction system for neutralization or solubilization in polymerization with a water-soluble polymerization initiator.

In polymerization of the cross-linkable polymer, a chain transfer agent may be further added in the polymerization process for regulation of the molecular weight after polymerization. The amount of the chain transfer agent added may be, for example, 0.1 to 5 mass % relative to the total of the entire monomers. With an amount of the chain transfer agent less than 0.1 mass %, the increased viscosity of the aqueous polymer composition may cause difficulty in handling in some cases, while with an amount of more than 5 mass %, the coating film may have insufficient water resistance in some cases. Examples of the chain transfer agent include mercaptans such as butyl mercaptan, n-dodecyl mercaptan and t-dodecyl mercaptan; alcohols such as methanol and isopropyl alcohol; α-methylstyrene dimer; and carbon tetrachloride.

The waterborne polymer dispersion may contain two or more of the cross-linkable polymers. The waterborne polymer dispersion may further contain a water-dispersible polymer and/or a water-soluble polymer other than the cross-linkable polymer.

In one aspect, for example, the waterborne polymer dispersion may contain a first polymer as cross-linkable polymer having an acid value of 20 mg KOH/g or more, and a second polymer having an acid value lower than that of the cross-linkable polymer.

Herein, though not required to have a cross-linkable group (aldo group, keto group, or epoxy group), the second polymer preferably has a cross-linkable group, more preferably has the same type of cross-linkable group as that of the cross-linkable polymer, from the viewpoint of further improving the properties of the coating film.

The acid value of the second polymer is preferably less than 25 mg KOH/g, more preferably less than 20 mg KOH/g, furthermore preferably less than 18 mg KOH/g.

The acid value of the polymer component of the waterborne polymer dispersion is preferably 1 to 250 mg KOH/g, more preferably 5 to 200 mg KOH/g, furthermore preferably 5 to 100 mg KOH/g. In the above aspect, the acid value and the content ratio of the cross-linkable polymer and the second polymer are prepared such that the acid value of the polymer component is controlled within the range.

In the above aspect, preferably the number average molecular weight of the second polymer is greater than the number average molecular weight of the cross-linkable polymer. The number average molecular weight of the second polymer is preferably 50000 to 2000000, more preferably 100000 to 1000000.

In the above aspect, the mass ratio of the content $Y_1$ of the cross-linkable polymer to the content $Y_2$ of the second polymer in the polymer component of a waterborne polymer dispersion, i.e. $Y_1/Y_2$, is preferably 1/99 to 90/10, more preferably 5/95 to 60/40, furthermore preferably 5/95 to 40/60. With a ratio of content $Y_1$ of the cross-linkable polymer of 1 or more, a coating film excellent in stain resistance can be produced, while with a ratio of content $Y_1$ of 90 or less, a coating film further excellent in water resistance can be produced. In other words, with a ratio $Y_1/Y_2$ in the range, both of further excellent water resistance and stain resistance can be achieved.

The Tg of the polymer component of a waterborne polymer dispersion is preferably 60° C. or lower (−65° C. or higher), more preferably 50° C. or lower, furthermore preferably 40° C. or lower. The aqueous polymer composition thus has excellent film forming properties; and the flexibility and the stain resistance of a coating film are improved in good balance.

The waterborne polymer dispersion containing two or more polymers as polymer components may contain emulsion particles composed of respective polymers, or may contain multi-component emulsion particles formed of two or more polymers.

Herein, a waterborne polymer dispersion containing two polymers can be obtained, for example, by the following method.

(Method 1)

The method includes separately polymerizing a polymer (a) and a polymer (b) so as to prepare a polymer (a) emulsion and a polymer (b) emulsion, respectively, which are mixed to obtain a waterborne polymer dispersion. In this method, a simple mixture of emulsion particles formed of the polymer (a) and emulsion particles formed of the polymer (b) is produced.

(Method 2)

The method includes performing emulsion polymerization or mini-emulsion polymerization of monomers so as to obtain a polymer (b) in an aqueous medium containing a polymer (a), thereby obtaining a waterborne polymer dispersion. In this method, a waterborne polymer dispersion containing multilayered emulsion particles having a central core of the polymer (a) of which the circumference is formed of the polymerized polymer (b).

In the method 2, the polymer (a) may be dispersed in an aqueous medium to form an emulsion, or may be dissolved in an aqueous medium. The polymer (a) may be obtained in a dispersed form in an aqueous medium by emulsion polymerization or mini-emulsion polymerization, or may be dispersed or dissolved in an aqueous medium after synthesis by solution polymerization.

In the method 2, when one of the polymer (a) and the polymer (b) is anionic, another is preferably anionic or nonionic; while when one is cationic, another is preferably cationic or nonionic.

(Method 3)

The method includes the successive steps of: preparing a polymer (a) by polymerization in a first stage; performing emulsion polymerization or mini-emulsion polymerization of monomers under presence of the produced polymer (a) in a second stage to obtain a polymer (b); and performing a second polymerization of the polymer (a) in a third stage after solubilizing treatment as needed. On this occasion, the monomer composition for the first polymerization of the polymer (a) and the monomer composition for the second polymerization of the polymer (a) may be different, so that a waterborne polymer dispersion contains three types of polymers.

In the above aspect, in the method 3 for producing a waterborne polymer dispersion, the case having the polymer (a) as the second polymer and the polymer (b) as the cross-linkable polymer is particularly preferred. On this occasion the cross-linkable polymer and the second polymer are more preferably anionic.

One embodiment of the method for producing the waterborne polymer dispersion in the above aspect is shown in the following.

In the present embodiment, the second polymer can be obtained by emulsion polymerization using an emulsifier. In production of the second polymer of anionic polymer, an anionic surfactant and/or a nonionic surfactant is used as emulsifier. More specifically, the surfactants described for use in emulsion polymerization to obtain the cross-linkable polymer can be used in the same way.

In production of the second polymer of cationic polymer, a cationic surfactant and/or a nonionic surfactant is used as emulsifier. More specifically, the surfactants described for use in emulsion polymerization to obtain the cross-linkable polymer can be used in the same way.

The amount of the emulsifier (surfactant) for use is preferably 0.05 to 25 mass % relative to the total mass of the monomers for producing a second polymer. Emulsion polymerization can be performed according to the conventional conditions without specific limitations.

In polymerization of the second polymer, a chain transfer agent may be added in the polymerization process for regulation of the molecular weight after polymerization. The amount of the chain transfer agent added may be, for example, 0.1 to 5 mass % relative to the total of the entire monomers. With an amount of the chain transfer agent less than 0.1 mass %, the increased viscosity of the aqueous polymer composition may cause difficulty in handling in some cases, while with an amount of more than 5 mass %, the coating film may have insufficient water resistance in some cases. Examples of the chain transfer agent include mercaptans such as butyl mercaptan, n-dodecyl mercaptan and t-dodecyl mercaptan; alcohols such as methanol and isopropyl alcohol; α-methylstyrene dimer; and carbon tetrachloride.

An alkali component may be added to an anionic second polymer, while an acid component may be added to a cationic second polymer. The dispersion stability of the aqueous polymer composition can be thus improved. The amount of the alkali component or the acid component added is preferably controlled such that the waterborne polymer dispersion has a pH in the range of 3 to 10. The dispersion stability can be thus further improved.

Although a conventional alkali such as sodium hydroxide, potassium hydroxide, and ammonia may be used as the alkali component without particular limitations, preferred examples include monoethanolamine, N,N-dimethyl ethanolamine, N,N-diethyl ethanolamine, diethanolamine, N-n-butyl diethanolamine, triisopropanolamine, and morpholines such as morpholine and 4-morpholinoethanol, particularly from the viewpoint of improving the water resistance of a coating film after drying. Among them, ammonia is particularly preferred as a volatile alkali component.

On the other hand, examples of the acid component include hydrochloric acid, sulfuric acid, nitric acid, methanesulfonic acid, p-toluenesulfonic acid, acetic acid, lactic acid, and hydroxyacetic acid.

Addition of the alkaline component or the acid component may be performed prior to polymerization, during polymerization, or after polymerization. The organic solvent usable in solubilization treatment may be auxiliarily used when water-solubility is insufficiently achieved with addition of the alkali component or the acid component only, or may be used alone for solubilization.

In the present embodiment of the production method, in order to allow the second polymer to retain a carboxylic acid group, an ethylenically unsaturated carboxylic acid monomer may be used as a part of monomers for use in polymerization. Examples of the ethylenically unsaturated carboxylic acid unit include acrylic acid, methacrylic acid, itaconic acid, fumaric acid, maleic acid, maleic anhydride, itaconic anhydride, fumaric acid, and a half-ester of maleic acid. The second polymer containing a carboxylic acid group is also useful in formation of a ring-opened epoxy group from an epoxy group.

The same monomers as those for use in obtaining the cross-linkable polymer may be used for obtaining the second polymer, and examples thereof include ethylenically unsaturated monomers having at least one aldo group or keto group in the molecule, other ethylenically unsaturated monomers, ethylenically unsaturated monomers for introducing a cationic group, etc. Although an ethylenically unsaturated monomer having an aldo group or keto group may not be necessarily used in production of the second polymer, the use in an amount of preferably 0.5 mass % or more, more preferably 0.5 mass % or more and 20 mass % or less, relative to the total of monomers is performed from the viewpoint of further improving the performance of a coating film with increased cross-linking points.

In the method 3 for producing a waterborne polymer dispersion in the above aspect, the case having the polymer (a) of a second polymer and the polymer (b) of a cross-linkable polymer is particularly preferred as described above. A specific aspect thereof is exemplified in the following.

In this aspect, first, a monomer mixture including 0 to 3 wt. % of an ethylenically unsaturated carboxylic acid monomer, 0 to 20 wt. % of an ethylenically unsaturated monomer having an aldo group or keto group, and 77 to 99.5 wt. % of other monomers is emulsion-polymerized in a first stage so as to obtain an emulsion of the second polymer (which was polymerized in the first time). Subsequently, a monomer mixture including 3 to 50 wt. % of an ethylenically unsaturated carboxylic acid monomer, 0.5 to 20 wt. % of an ethylenically unsaturated monomer having an aldo group or keto group, and 30 to 97 wt. % of other monomers is emulsion-polymerized under presence of the first-time second polymer in a second stage so as to obtain an emulsion including the first-time second polymer and a cross-linkable polymer. After addition of an alkali component to the emulsion, a monomer mixture including 0 to 3 wt. % of an ethylenically unsaturated carboxylic acid monomer, 0 to 20 wt. % of an ethylenically unsaturated monomer having an aldo group or keto group, and 77 to 99.5 wt. % of other monomers is emulsion-polymerized in the emulsion in the subsequent third stage so as to obtain the second polymer (which was polymerized in the second time). An emulsion containing the second polymer (first-time), the cross-linkable polymer, and the second polymer (second-time) can be thus obtained through the three stages.

Although polymerization is performed through three stages in the above aspect, further multi-stage polymerization may be performed in the present invention, corresponding to the purpose. Through multi-stage polymerization, a coating film obtained from the aqueous polymer composition tends to have further improved performance for preventing whitening when immersed in water.

<Aqueous Polymer Composition>

The aqueous polymer composition of the present aspect is a composition obtained by blending a cross-linking agent and a waterborne polymer dispersion. The aqueous polymer composition may include a component other than the cross-linking agent and the waterborne polymer dispersion.

In order to improve the long-term storage stability, the pH of the aqueous polymer composition is preferably in the range of 5 to 10. As a pH adjusting agent to adjust the pH in the range, for example, ammonia, sodium hydroxide, potassium hydroxide, and amines such as dimethylaminoethanol may be used.

The mass ratio of the dispersoid (solid content) to the dispersion medium (aqueous medium) in the aqueous polymer composition is preferably 70/30 or less, more preferably 30/70 or more and 65/35 or less.

Examples of the aqueous medium for dispersing and/or dissolving the cross-linkable polymer and the like in the aqueous polymer composition include water and a mixed solvent of water and alcohols.

The aqueous polymer composition may include components to be typically blended in a waterborne paint or the like, such as a coalescing agent, a thickener, a defoamer, a pigment, a dispersant, a dye, and a preservative; and components other than the above such as an ultraviolet absorber, an optical stabilizer, and inorganic colloidal particles may be optionally blended.

The colloidal inorganic particles effective to further improve stain resistance may be blended in an amount of preferably 1 to 80 parts by mass, more preferably 2 to 15 parts by mass relative to the total 100 parts by mass of the polymer components in a waterborne polymer dispersion. With a blending ratio of colloidal inorganic particles within the range, the coating film to be produced is hardly whitened even when immersed in water.

Further, an ultraviolet absorber or an optical stabilizer is preferably contained in the aqueous polymer composition for imparting high weather resistance. As a method for containing the ultraviolet absorber or the optical stabilizer in the aqueous polymer composition, the absorber or the stabilizer may be mixed with a coalescing agent and the like prior to addition, though the presence thereof during emulsion polymerization for obtaining the waterborne polymer dispersion is more suitable. The ultraviolet absorber or the optical stabilizer may be added in an amount of 0.1 mass % to 5 mass % relative to the total amount of the monomers to produce the cross-linkable polymer, in production of the cross-linkable polymer.

Further, a radically polymerizable ultraviolet absorber having a radically polymerizable double bond in the molecule may be used as the ultraviolet absorber, and a radically polymerizable optical stabilizer having a radically polymerizable double bond in the molecule may be used as the optical stabilizer. Use of an ultraviolet absorber and an optical stabilizer in combination further improves the weather resistance of a coating film to be produced.

Examples of the ultraviolet absorber include a benzotriazole ultraviolet absorber, a radically polymerizable benzotriazole ultraviolet absorber, and a triazine ultraviolet absorber.

Examples of the benzotriazole ultraviolet absorber include 2-(2'-hydroxy-5'-methylphenyl)benzotriazole, 2-(2'-hydroxy-5'-tert-butylphenyl)benzotriazole, 2-(2-hydroxy-3,5-di-tert-butylphenyl)benzotriazole, 2-(2-hydroxy-5-tert-octylphenyl)benzotriazole, 2-(2-hydroxy-3,5-bis(α,α'-dimethylbenzyl)phenyl]benzotriazole), a condensate of methyl-3-[3-tert-butyl-5-(2H-benzotriazol-2-yl)-4-hydroxyphenyl]propionate and polyethylene glycol (molecular weight: 300) (made by BASF Japan Ltd., product name: TINUVIN 1130), isooctyl-3-[3-(2H-benzotriazol-2-yl)-5-tert-butyl-4-hydroxyphenyl]propionate (made by BASF Japan Ltd., product name: TINUVIN 384), 2-(3-dodecyl-5-methyl-2-hydroxyphenyl)benzotriazole (made by BASF Japan Ltd., product name: TINUVIN 571), 2-(2'-hydroxy-3'-tert-butyl-5'-methylphenyl)-5-chlorobenzotriazole 2-(2'-hydroxy-3',5'-di-tert-amylphenyl)benzotriazole, 2-(2'-hydroxy-4'-octoxyphenyl)benzotriazole, 2-[2-hydroxy-3'-(3",4",5",6"-tetrahydrophthalimide methyl)-5'-methylphenyl]benzotriazole, 2,2-methylenebis[4-(1,1,3,3-tetramethylbutyl)-6-(2H-benzotriazol-2-yl)phenol], and 2-(2H-benzotriazol-2-yl)-4,6-bis(1-methyl-1-phenylethyl)phenol (made by BASF Japan Ltd., product name: TINUVIN 900).

Further, examples of the radically polymerizable benzotriazole ultraviolet absorber include 2-(2'-hydroxy-5'-methacryloxyethylphenyl)-2H-benzotriazole (manufactured by Otsuka Chemical Co., Ltd., product name: RUVA-93), 2-(2'-hydroxy-5'-methacryloxyethyl-3-tert-butylphenyl)-2H-benzotriazole, 2-(2'-hydroxy-5'-methacryloxypropyl-3-tert-butyl-phenyl)-5-chloro-2H-benzotriazole, and 3-methacryloyl-2-hydroxypropyl-3-[3'-(2"-benzotriazolyl)-4-hydroxy-5-tert-butyl]phenylpropionate (made by BASF Japan Ltd., product name: CGL-104).

Further, examples of the triazine ultraviolet absorber include TINUV400 (product name, made by BASF Japan, Ltd.).

Examples of the optical stabilizer include a hindered amine optical stabilizer and a radically polymerizable hindered amine optical stabilizer.

The hindered amine optical stabilizer preferably has low basicity, specifically with a base dissociation constant (pKb) of 8 or more. More specifically, examples thereof include bis(2,2,6,6-tetramethyl-4-piperidyl)succinate, bis(2,2,6,6-tetramethyl-piperidyl)sebacate bis(1,2,2,6,6-pentamethyl-4-piperidyl)2-(3,5-di-tert-butyl-4-hydroxybenzyl)-2-butylmalonate, 1-[2-[3-(3,5-di-tert-butyl-4-hydroxyphenyl)propynyloxy]ethyl]-4-[3-(3,5-di-tert-butyl-4-hydroxyphenyl)propynyloxy]-2,2,6,6-tetramethylpiperidine, a mixture of bis(1,2,2,6,6-pentamethyl-4-piperidyl)sebacate and methyl-1,2,2,6,6-pentamethyl-4-piperidyl-sebacate (made by BASF Japan Ltd., product name: TINUVIN 292), bis(1-octoxy-2,2,6,6-tetramethyl-4-piperidyl)sebacate, and TINUVIN 123 (product name, made by BASF Japan Ltd.).

Examples of the radically polymerizable hindered amine photo stabilizer include 1,2,2,6,6-pentamethyl-4-piperidyl methacrylate, 1,2,2,6,6-pentamethyl-4-piperidyl acrylate, 2,2,6,6-tetramethyl-4-piperidyl methacrylate, 2,2,6,6-tetramethyl-4-piperidyl acrylate, 1,2,2,6,6-pentamethyl-4-iminopiperidyl methacrylate, 2,2,6,6,-tetramethyl-4-iminopiperidyl methacrylate, 4-cyano-2,2,6,6-tetramethyl-4-piperidyl methacrylate, and 4-cyano-1,2,2,6,6-pentamethyl-4-piperidyl methacrylate.

The aqueous polymer composition also may contain a polymer dispersion stabilizer such as (partially saponified) polyvinyl alcohol, methyl cellulose, hydroxyethyl cellulose, and polyvinyl pyrrolidone; a thickener such as polyether thickener; a plasticizer; and a coalescing agent; which may be used in combination.

Further, the aqueous polymer composition may include components to be added and blended in typical paints, various coating materials and the like, such as a viscosity adjusting agent, a pH adjusting agent, a defoamer, a pigment, a filler, a dispersant, a dye, a preservative, a surfactant, a heat stabilizer, an ultraviolet absorber, an antioxidant, an optical stabilizer, a flame retardant, an organic solvent, a moistening agent, a surfactant, a thickener, a plasticizer, a coalescing agent, and an anti-rust agent. These may be dispersed in the aqueous polymer composition with use of a kneading machine such as an attritor and a sand mill, such that the aqueous polymer composition has a predetermined viscosity corresponding to application.

The aqueous polymer composition is applied, for example, onto a substrate and dried to form a coating film. The coating film contains a cross-linked product obtained by cross-linking cross-likable polymer with a cross-linking agent.

In the present aspect, since the cross-linkable polymer and the cross-linking agent have specific compositions as described above, the coating film produced therefrom is excellent in hardness, stain resistance, water resistance, and alkali yellowing resistance.

(Composite)

A composite in the present embodiment is described in the following. The composite in the present embodiment includes a substrate and a coating film of the aqueous polymer composition formed on at least one face of the substrate.

Examples of the substrate material include: an nonmetallic inorganic material such as glass, plaster, and stone; a metal such as iron, stainless steel, aluminum, and copper; a polymer such as acryl, polystyrene, polyesters, polycarbonate, and polyolefin; synthetic rubber, natural rubber, cotton, silk, hemp, fiber of nylon or the like; and wood.

A coating film may be formed by directly applying the aqueous polymer composition to a substrate, or may be formed by applying a paint or a coating material on a substrate and further applying the aqueous polymer composition thereon.

Although the preferred embodiments of the present invention have been described above, the present invention is not limited to the above embodiments.

EXAMPLES

The following Examples more specifically illustrate the present invention, but the present invention is not limited to the Examples.

The analysis area ratios of the semicarbazide compositions (a), (b-1), (b-2) and (b-3) were obtained according to the method described above, with a wavelength of ultraviolet-visible absorption detector of 200 nm. Since isophorone diisocyanate includes a plurality of stereoisomers, the peak areas $S_A$, $S_{B-1}$, $S_{B-2}$, and $S_{B-3}$ were obtained as the area of a group of peaks as sum of the peaks derived from the respective isomers.

Yellowing of the coating film with an aqueous alkaline solution was detected by measuring the change in color after immersion of the coating film in a saturated calcium hydroxide solution for a predetermined period of time. More specifically, a white enamel paint was applied to a flexible board to prepare a dried coated board, on which the aqueous polymer composition was applied such that the coating liquid have a thickness of 250 μm, which was dried at room temperature to make a measurement sample. The measurement sample was immersed in a saturated calcium hydroxide solution at 23° C. for 1 week and subjected to measurement of the change in color. In measurement of the change in color, L, a, b values were measured with a color-difference meter CR-200 made by Minolta before and after the testing (before and after the immersion in a saturated calcium hydroxide solution), and the variation in the b value before and after the testing was indicated by Δb value.

The validation testing of the cross-linking condition of a coating film was performed by immersing the coating film in an organic solvent and measuring the insoluble portion. In the specific measurement method, a coating film having a thickness of about 100 μm was immersed in acetone for 24 hours and dried for measurement of the rate of change in mass before and after the immersion.

Synthesis Example 1-1

<Adjustment of Polycarbonyl Compounds>

A reaction vessel having a reflux condenser, a dripping tank, a thermometer, and a stirrer was charged with 218 g of ion-exchanged water and 3.7 g of 25% aqueous solution of a surfactant (trade name: ADEKARIA SOAP SE-1025N, made by ADEKA Corporation), and after raising the temperature in the reaction vessel to 80° C., a mixture solution of 9 g of methacrylic acid, 4.5 g of styrene, 234 g of butyl acrylate, 13.5 g of diacetone acrylamide, 189 g of methyl methacrylate, 0.45 g of dodecyl mercaptan, 225 g of ion-exchanged water, 14.4 g of ADEKARIA SOAP SE-1025N, 10 g of 25% aqueous solution of polyoxyethylene nonylphenyl ether (trade name: EMULGEN 950, made by Kao Corporation), and 1 g of ammonium persulfate was flowed into the reaction vessel from a dripping tank for 3 hours. During inflow, the temperature in the reaction vessel was kept at 80° C. After completion of the inflow, the temperature in the reaction vessel was kept at 80° C. for 2 hours. Subsequently the content was cooled to room temperature, to which 25% ammonia aqueous solution was added for adjusting the pH at 7.5. The content was then subjected to filtration with a 100 mesh screen so as to produce a waterborne polymer dispersion of carbonyl group-containing copolymer having a solid content of 46.8% and an average particle diameter of 106 nm.

To the waterborne polymer dispersion, 2% CS-12 (made by JNC Corporation) was added, the resulting coating liquid was thoroughly stirred and mixed to produce a coating film having a thickness of about 100 μm, which was dried at 23° C. for 1 week. The produced coating film was immersed in acetone for 24 hours and dried for measurement of the rate of change in mass before and after the immersion. The measurement results showed that the insoluble portion of the coating film was 8%.

Example 1-1

(Semicarbazide Composition)

A reaction vessel having a reflux condenser, a thermometer, and a stirrer was charged with 22.0 g of hydrazine monohydrate, 200 g of tetrahydrofuran (water-soluble organic solvent), and 60 g of water. Subsequently, a mixture solution of 400 g of toluene (water-insoluble solvent) and 50 g of isophorone diisocyanate was added dropwise at room temperature over a time period of 1 hour. Subsequently, stirring was performed at room temperature for 1 hour so as to complete the reaction (the ratio of water-soluble organic solvent excluding water at the end of reaction: 67%). Subsequently the organic solvent and water were removed under reduced pressure at a temperature of 50° C. or lower. The produced white powder was vacuum dried at room temperature so as to produce 64 g of a semicarbazide composition.

The semicarbazide composition was dissolved in the same amount of water to make a 50% aqueous solution.

The LC/MS analysis of the semicarbazide composition resulted in an analysis area ratio (a) of 0.09%, an analysis area ratio (b-1) of 85.20%, an analysis area ratio (b-2) of 11.53%, and analysis area ratio (b-3) of 3.18%. The molecular weight per semicarbazide group calculated from the ratios is 167. The chromatogram obtained by the LC/MS analysis is shown in FIG. 1.

(Aqueous Polymer Composition and Coating Film)

To 100 g of the carbonyl group-containing waterborne copolymer dispersion in the Synthesis Example 1-1, 2% CS-12 (made by JNC Corporation) was added and then thoroughly stirred and mixed. Subsequently, 2.40 g of 50% aqueous solution of the semicarbazide composition (semicarbazide group relative to keto group: 0.9 equivalent) was added and mixed to make an aqueous polymer composition. The produced aqueous polymer composition had both of cold curing ability and storage stability.

The coating solution of the aqueous polymer composition was applied to a thickness of about 100 μm and dried at 23° C. for 1 week to obtain a coating film. The produced coating film was immersed in acetone for 24 hours and dried for measurement of the rate of change in mass before and after the immersion. The measurement results showed that the insoluble portion of the coating film was 88%.

Further, a white enamel paint was applied to a flexible board to prepare a dried coated board, on which the aqueous polymer composition was applied to a thickness of 250 μm, which was dried at room temperature for 1 week to make a coating film. The produced coating film was immersed in a saturated calcium hydroxide solution at 23° C. for 1 week, resulting in a low Δb value of 3.7.

Example 1-2

(Semicarbazide Composition)

A reaction vessel having a reflux condenser, a thermometer, and a stirrer was charged with 18.0 g of hydrazine monohydrate, 200 g of tetrahydrofuran, and 60 g of water. Subsequently, a mixture solution of 700 g of toluene and 50 g of isophorone diisocyanate was added dropwise at room temperature over a time period of 1 hour. Subsequently, stirring was performed at room temperature for 1 hour so as to complete the reaction (the ratio of water-soluble organic solvent excluding water at the end of reaction: 78%). Subsequently the organic solvent and water were removed under reduced pressure at a temperature of 50° C. or lower. The produced white powder was vacuum dried at room temperature so as to produce 61.5 g of a semicarbazide composition. The semicarbazide composition was dissolved in the same amount of water to make a 50% aqueous solution.

Figure 2:
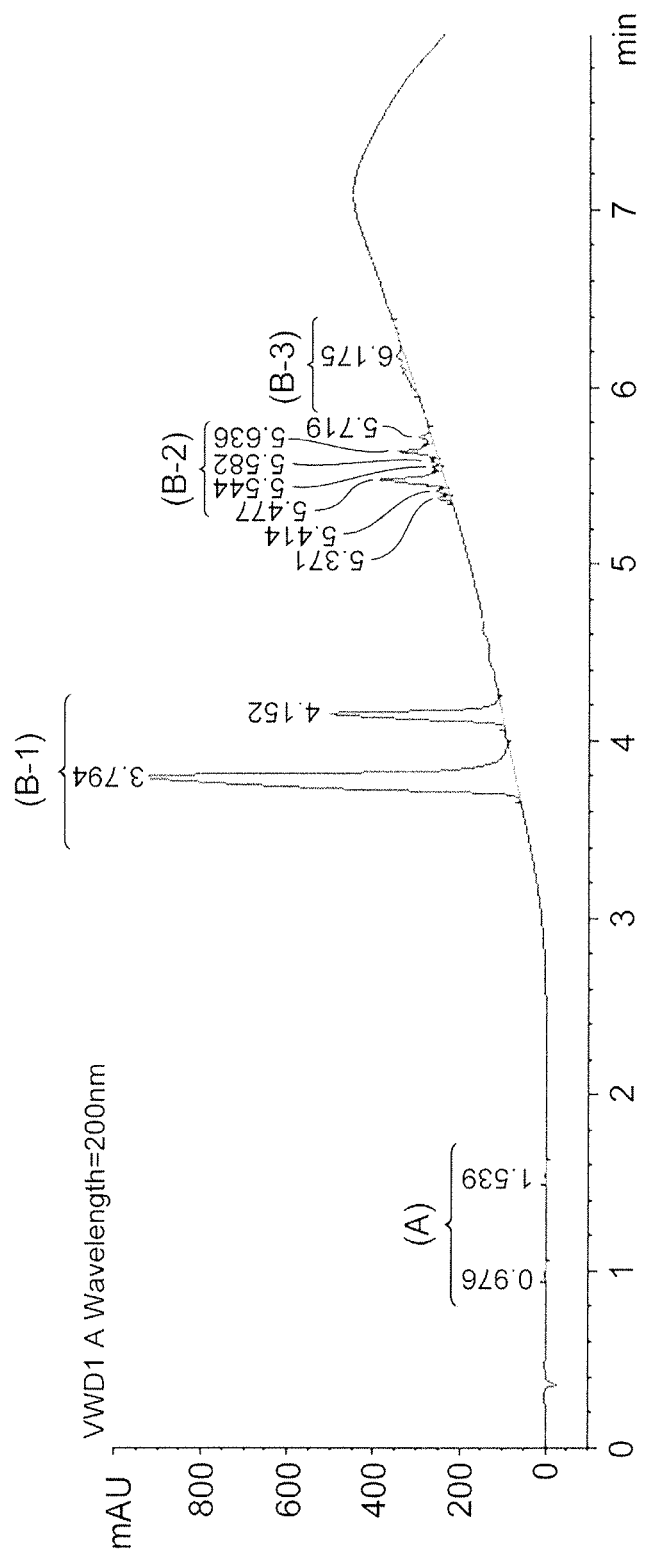
FIG. 2 is a chart showing the LC/MS analysis results of the semicarbazide composition obtained in Example 1-2.

The LC/MS analysis of the semicarbazide composition resulted in an analysis area ratio (a) of 0.01%, an analysis area ratio (b-2) of 81%, an analysis area ratio (b-2) of 15%, and analysis area ratio (b-3) of 4%. The molecular weight per semicarbazide group calculated from the ratios is 172. The chromatogram obtained by the LC/MS analysis is shown in FIG. 2.

(Aqueous Polymer Composition and Coating Film)

To 100 g of the carbonyl group-containing waterborne copolymer dispersion in the Synthesis Example 1-1, 2% CS-12 (made by JNC Corporation) was added and then thoroughly stirred and mixed. Subsequently, 2.48 g of 50% aqueous solution of the semicarbazide composition (semicarbazide group relative to keto group: 0.9 equivalent) was added and mixed to make an aqueous polymer composition. The produced aqueous rein composition had both of cold curing ability and storage stability.

The coating solution of the aqueous polymer composition was applied to a thickness of about 100 μm and dried at 23° C. for 1 week to obtain a coating film. The produced coating film was immersed in acetone for 24 hours and dried for measurement of the rate of change in mass before and after the immersion. The measurement results showed that the insoluble portion of the coating film was 90%.

Further, a white enamel paint was applied to a flexible board to prepare a dried coated board, on which the aqueous polymer composition was applied to a thickness of 250 μm, which was dried at room temperature for 1 week to make a coating film. The produced coating film was immersed in a saturated calcium hydroxide solution at 23° C. for 1 week, resulting in a low Δb value of 3.2.

Example 1-3

(Semicarbazide Composition)

A reaction vessel having a reflux condenser, a thermometer, and a stirrer was charged with 25.0 g of hydrazine monohydrate, 200 g of tetrahydrofuran, and 60 g of water. Subsequently, a mixture solution of 200 g of toluene and 50 g of isophorone diisocyanate was added dropwise at room temperature over a time period of 1 hour. Subsequently, stirring was performed at room temperature for 1 hour so as to complete the reaction (the ratio of water-soluble organic solvent excluding water at the end of reaction: 50%). Subsequently the organic solvent and water were removed under reduced pressure at a temperature of 50° C. or lower. The produced white powder was vacuum dried at room temperature so as to produce 64 g of a semicarbazide composition. The semicarbazide composition was dissolved in the same amount of water to make a 50% aqueous solution.

Figure 3:
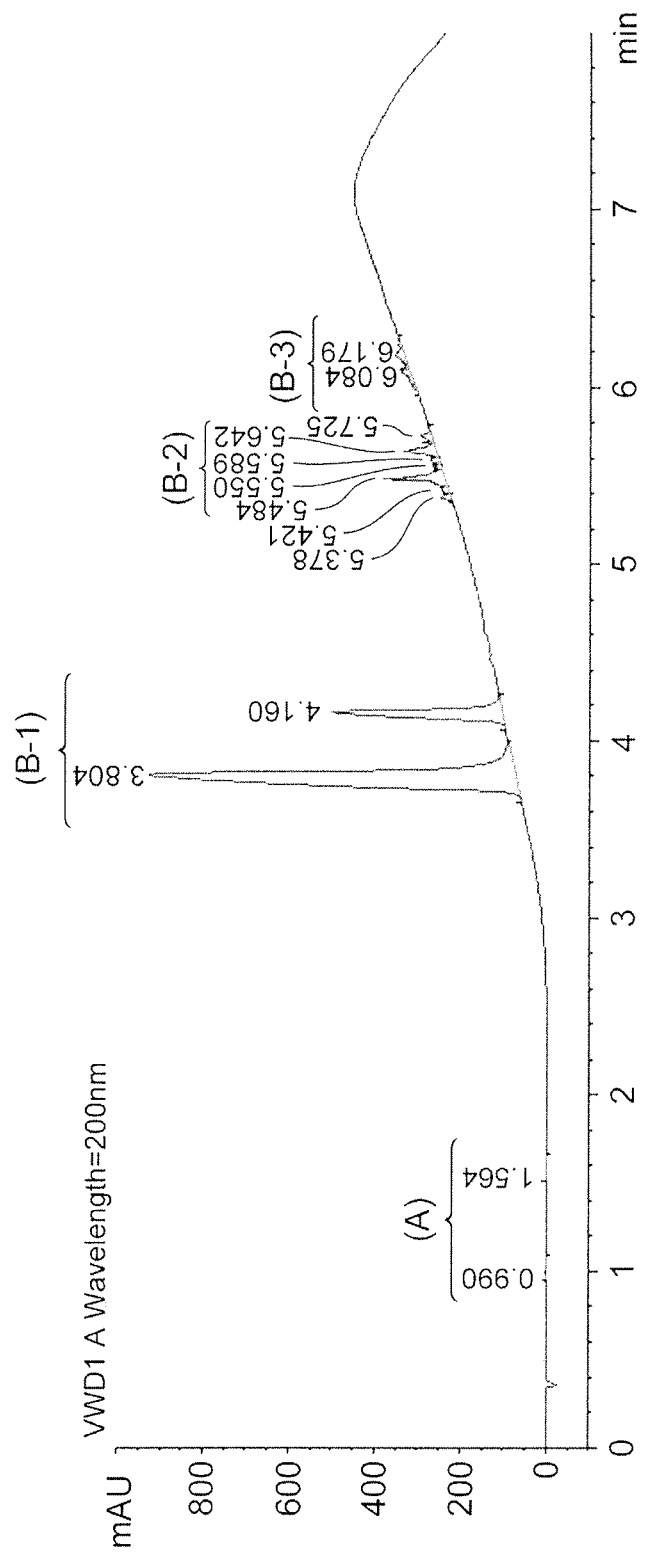
FIG. 3 is a chart showing the LC/MS analysis results of the semicarbazide composition obtained in Example 1-3.

The LC/MS analysis of the semicarbazide composition resulted in an analysis area ratio (a) of 0.21%, an analysis area ratio (b-1) of 89%, an analysis area ratio (b-2) of 9%, and analysis area ratio (b-3) of 1.8%. The molecular weight per semicarbazide group calculated from the ratios is 159. The chromatogram obtained by the LC/MS analysis is shown in FIG. 3.

(Aqueous Polymer Composition and Coating Film)

To 100 g of the carbonyl group-containing waterborne copolymer dispersion in the Synthesis Example 1-1, 2% CS-12 (made by JNC Corporation) was added and then thoroughly stirred and mixed. Subsequently, 2.28 g of 50% aqueous solution of the semicarbazide composition (semicarbazide group relative to keto group: 0.9 equivalent) was added and mixed to make an aqueous polymer composition. The produced aqueous rein composition had both of cold curing ability and storage stability.

The coating solution of the aqueous polymer composition was applied to a thickness of about 100 μm and dried at 23° C. for 1 week to obtain a coating film. The produced coating film was immersed in acetone for 24 hours and dried for measurement of the rate of change in mass before and after the immersion. The measurement results showed that the insoluble portion of the coating film was 86%.

Further, a white enamel paint was applied to a flexible board to prepare a dried coated board, on which the aqueous polymer composition was applied to a thickness of 250 μm, which was dried at room temperature for 1 week to make a coating film. The produced coating film was immersed in a saturated calcium hydroxide solution at 23° C. for 1 week, resulting in a low Δb value of 62.

Further, a white enamel paint was applied to an alumite board to prepare a dried coated board, on which the aqueous polymer composition was applied to a thickness of 100 μm, which was dried at room temperature for 1 week to make a coating film. The coated board with the four sides and the back side sealed with wax was immersed in 1 N sulfuric acid aqueous solution at 23° C. for 1 week, resulting in only a small amount of blisters on the coated face.

Comparative Example 1

(Semicarbazide Composition)

A reaction vessel having a reflux condenser, a thermometer, and a stirrer was charged with 120.0 g of hydrazine monohydrate, 200 g of tetrahydrofuran, and 1000 g of water. Subsequently, a mixture solution of 200 g of tetrahydrofuran and 50 g of isophorone diisocyanate was added dropwise at room temperature over a time period of 1 hour. Subsequently, stirring was performed at a temperature of 50° C. or lower for 1 hour so as to complete the reaction (the ratio of water-soluble organic solvent excluding water at the end of reaction: 0%). Subsequently the organic solvent and water were removed under reduced pressure at a temperature of 50° C. or lower. The produced white powder was vacuum dried at room temperature so as to produce 64 g of a semicarbazide composition. The semicarbazide composition was dissolved in the same amount of water to make a 50% aqueous solution.

Figure 4:
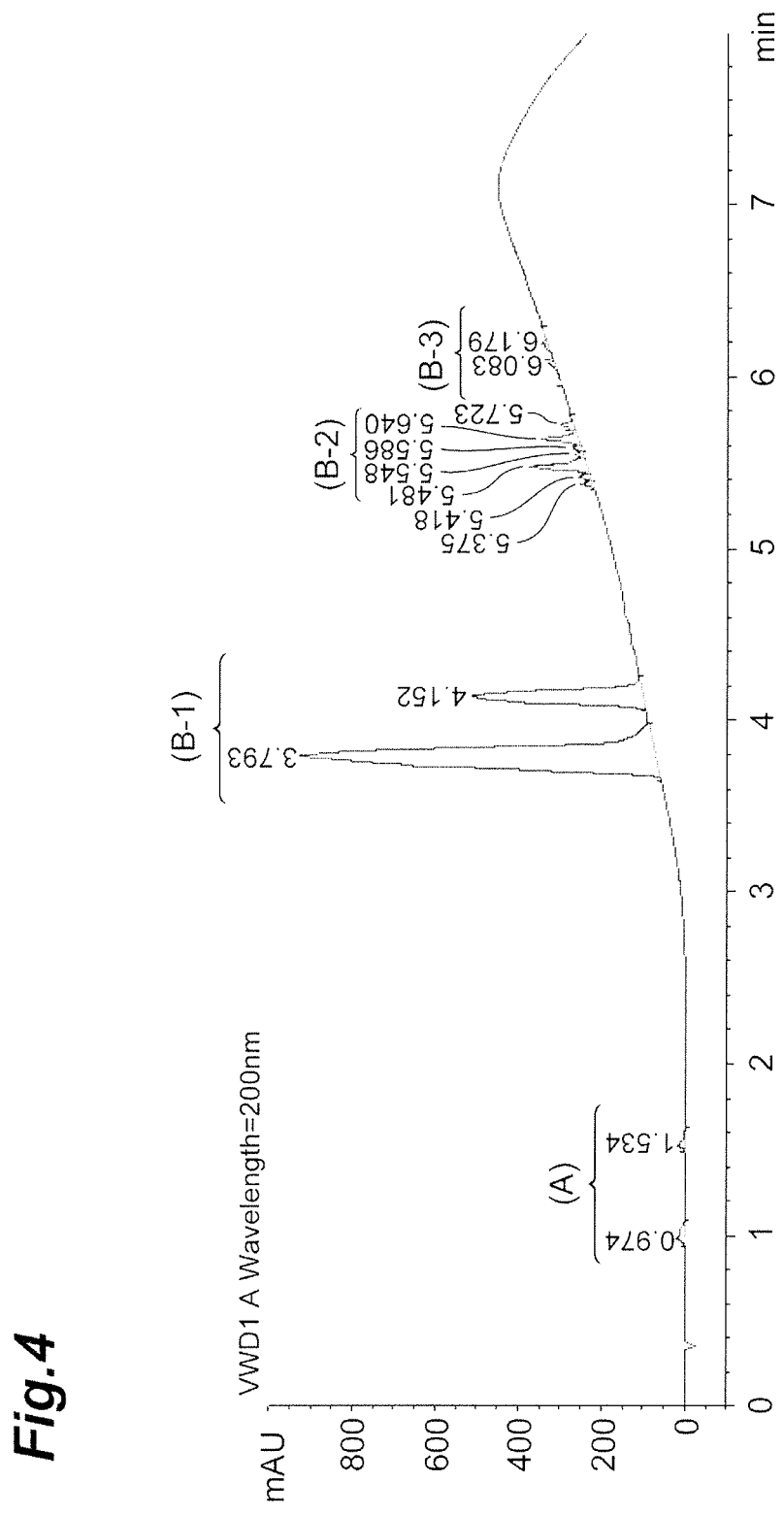
FIG. 4 is a chart showing the LC/MS analysis results of the semicarbazide composition obtained in Comparative Example 1-1.

The LC/MS analysis of the semicarbazide composition resulted in an analysis area ratio (a) of 2.2%, an analysis area ratio (b-1) of 92%, an analysis area ratio (b-2) of 5%, and analysis area ratio (b-3) of 1%. The molecular weight per semicarbazide group calculated from the ratios was 154. The chromatogram obtained by the LC/MS analysis is shown in FIG. 4.

(Aqueous Polymer Composition and Coating)

To 100 g of the carbonyl group-containing waterborne copolymer dispersion in the Synthesis Example 1-1, 2% CS-12 (made by JNC Corporation) was added and then thoroughly stirred. Subsequently, 2.21 g of 50% aqueous solution of the semicarbazide composition (semicarbazide group relative to keto group: 0.9 equivalent) was added and mixed to make an aqueous polymer composition.

The coating solution of the produced aqueous polymer composition was applied to a thickness of about 100 μm and dried at 23° C. for 1 week to obtain a coating film. The produced coating film was immersed in acetone for 24 hours and dried for measurement of the rate of change in mass before and after the immersion. The measurement results showed that the insoluble portion of the coating film was 87%.

Further, a white enamel paint was applied to a flexible board to prepare a dried coated board, on which the aqueous polymer composition was applied to a thickness of 250 μm, which was dried at room temperature for 1 week to make a coating film. The produced coating film was immersed in a saturated calcium hydroxide solution at 23° C. for 1 week, resulting in a high Δb value of 12.5.

Comparative Example 2

(Semicarbazide Composition)

A reaction vessel having a reflux condenser, a thermometer, and a stirrer was charged with 200 g of hydrazine monohydrate, 200 g of tetrahydrofuran. Subsequently, a mixture solution of 200 g of tetrahydrofuran and 50 g of isophorone diisocyanate was added dropwise at room temperature over a time period of 1 hour. Subsequently, stirring was performed at room temperature for 1 hour so as to complete the reaction (the ratio of water-soluble organic solvent excluding water at the end of reaction: 0%). Subsequently the organic solvent and water were removed under reduced pressure at a temperature of 50° C. or lower. The produced white powder was vacuum dried at room temperature so as to produce 64 g of a semicarbazide composition. The semicarbazide composition was dissolved in the same amount of water to make a 50% aqueous solution.

Figure 5:
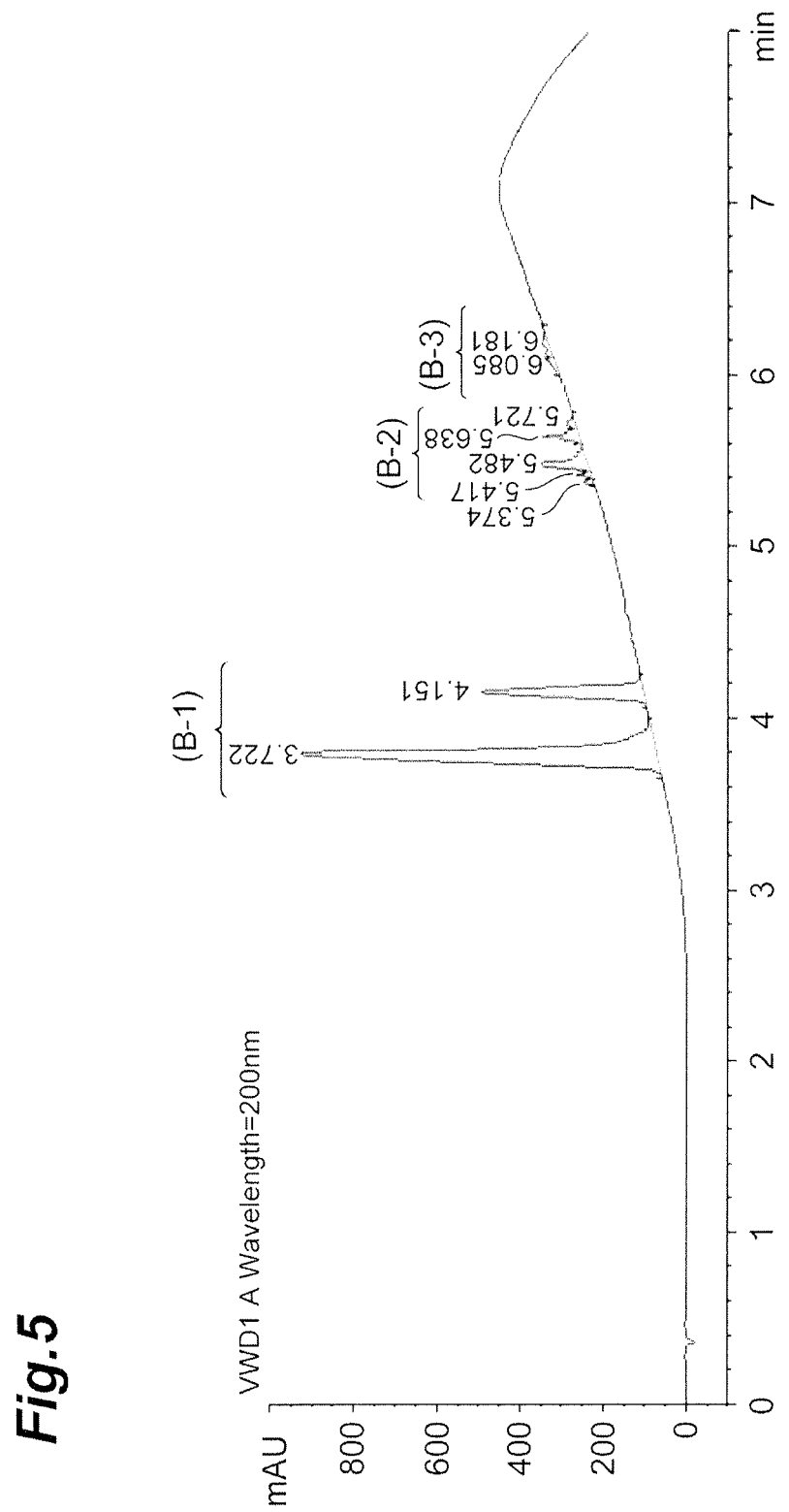
FIG. 5 is a chart showing the LC/MS analysis results of the semicarbazide composition obtained in Comparative Example 1-2.

The LC/MS analysis of the semicarbazide composition resulted in an analysis area ratio (a) of 0.000%, i.e., below detection limit, an analysis area ratio (b-1) of 95%, an analysis area ratio (b-2) of 4.5%, and analysis area ratio (b-3) of 0.5%. The molecular weight per semicarbazide group calculated from the ratios was 150. The chromatogram obtained by the LC/MS analysis is shown in FIG. 5.

(Aqueous Polymer Composition and Coating Film)

To 100 g of the carbonyl group-containing waterborne copolymer dispersion in the Synthesis Example 1-1, 2% CS-12 (made by JNC Corporation) was added and then thoroughly stirred and mixed. Subsequently, 2.15 g of 50% aqueous solution of the semicarbazide composition (semicarbazide group relative to keto group: 0.9 equivalent) was added and mixed to make an aqueous polymer composition. The coating solution of the produced aqueous polymer composition was applied to a thickness of about 100 μm and dried at 23° C. for 1 week to obtain a coating film. The produced coating film was immersed in acetone for 24 hours and dried for measurement of the rate of change in mass before and after the immersion. The measurement results showed that the insoluble portion of the coating film was 85%.

Further, a white enamel paint was applied to a flexible board to prepare a dried coated board, on which the aqueous polymer composition was applied to a thickness of 250 μm, which was dried at room temperature for 1 week to make a coating film. The produced coating film was immersed in a saturated calcium hydroxide solution at 23° C. for 1 week, resulting in a Δb value of 3.1.

Further, a white enamel paint was applied to an alumite board to prepare a dried coated board, on which the aqueous polymer composition was applied to a thickness of 100 μm, which was dried at room temperature for 1 week to make a coating film. The coated board with the four sides and the back side sealed with wax was immersed in 1 N sulfuric acid aqueous solution at 23° C. for 1 week, resulting in a large amount of blisters on the coated face.

The method for measuring the number average molecular weight is as follows.

Using gel permeation chromatography, determination was based on the standard polystyrene calibration curve.

(Equipment Used)

Liquid chromatography equipment: HLC-8020 manufactured by Tosoh Corporation.

Column: TSKgel G-5000 HXL, TSKgel G-4000 HXL, and TSKgel G-2000 HXL, made by Tosoh Corporation Data processing equipment: SC 8010 made by Tosoh Corporation Carrier: tetrahydrofuran Production Example 2-1

A reaction vessel having a reflux condenser, a thermometer, and a stirrer was charged with 22.0 g of hydrazine monohydrate, 200 g of tetrahydrofuran, and 60 g of water. Subsequently, a mixture solution of 400 g of toluene and 50 g of isophorone diisocyanate was added dropwise at room temperature over a time period of 1 hour. Subsequently, stirring was performed at room temperature for 1 hour so as to complete the reaction (the ratio of non-water-insoluble organic solvent excluding water at the end of reaction: 67%). Subsequently the organic solvent and water were removed under reduced pressure at a temperature of 50° C. or lower. The produced white powder was vacuum dried at room temperature so as to produce 64 g of a semicarbazide composition. The semicarbazide composition was dissolved in the same amount of water to make a 50% aqueous solution.

The LC/MS analysis of the semicarbazide composition resulted in an analysis area ratio (a) of 0.09%, an analysis area ratio (b-1) of 85.20%, an analysis area ratio (b-2) of 11.53%, and analysis area ratio (b-3) of 3.18%. The molecular weight per semicarbazide group calculated from the ratios is 167.

Production Example 2-2: Production of Waterborne Polymer Dispersion A-1

A reaction vessel having a reflux condenser, a dripping tank, a thermometer, and a stirrer was charged with 509.4 g of ion-exchanged water and 3.5 g of 25% aqueous solution of a surfactant AQUALON KH-10, and after raising the temperature in the reaction vessel to 80° C., a mixture solution of 11.2 g of methyl methacrylate, 67.2 g of butyl acrylate, 40.0 g of butyl methacrylate, 16.0 g of acrylic acid, 16.0 g of methacrylic acid, 9.6 g of diacetone acrylamide, 1.6 g of n-dodecyl mercaptan, 110.0 g of ion-exchanged water, 3.2 g of 25% aqueous solution of surfactant (trade name: AQUALON KH-10, made by Dai-ichi Kogyo Seiyaku Co., Ltd.), and 36.0 g of 2% aqueous solution of ammonium persulfate was flowed into the reaction vessel from a dripping tank over a time period of 40 minutes, while keeping the temperature in the reaction vessel at 80° C. during inflow. After completion of the inflow, the temperature in the reaction vessel was kept at 80° C. for 30 minutes, and the pH was adjusted to 7 with 25% aqueous ammonia, so as to make a dispersion liquid of the polycarbonyl compound. A portion of the produced polycarbonyl compound was sampled for measurement of the number average molecular weight and the acid value, resulting in a number average molecular weight of 29000 and an acid value of 283.

Subsequently, under presence of the dispersion liquid of polycarbonyl compound, a mixture solution of 59.2 g of methyl methacrylate, 149.6 g of butyl acrylate, 240.0 g of butyl methacrylate, 2.4 g of methacrylic acid, 28.8 g of diacetone acrylamide, 0.24 g of n-dodecyl mercaptan, 267.0 g of ion-exchanged water, 10.4 g of 25% aqueous solution of AQUALON KH-10, and 72.0 g of 2% aqueous solution of ammonium persulfate was flowed into the reaction vessel from a dripping tank over a time period of 2 hours, while keeping the temperature in the reaction vessel at 80° C. during inflow. After completion of the inflow, the temperature in the reaction vessel was kept at 80° C. for 60 minutes for polymerization of the polymer (second polymer). Subsequently the content was cooled to room temperature, with a pH adjusted to 7.5 with addition of 25% aqueous ammonia, and then subjected to filtration with a 100 mesh screen, so that a waterborne polymer dispersion A-1 having a solid content of 40.0% and an average particle diameter of 186 nm was obtained.

Production Example 2-3: Production of Waterborne Polymer Dispersion A-2

A reaction vessel having a reflux condenser, a dripping tank, a thermometer, and a stirrer was charged with 509.4 g of ion-exchanged water and 3.5 g of 25% aqueous solution of a surfactant (trade name: AQUALON KH-10, made by Dai-ichi Kogyo Seiyaku Co., Ltd.), and after raising the temperature in the reaction vessel to 80° C., a mixture solution of 59.2 g of methyl methacrylate, 149.6 g of butyl acrylate, 240.0 g of butyl methacrylate, 2.4 g of methacrylic acid, 28.8 g of diacetone acrylamide, 0.24 g of n-dodecyl mercaptan, 283.4 g of ion-exchanged water, 19.2 g of 25% aqueous solution of AQUALON KH-10, and 84.0 g of 2% aqueous solution of ammonium persulfate was flowed into the reaction vessel from a dripping tank over a time period of 2 hours, while keeping the temperature in the reaction vessel at 80° C. during inflow. After completion of the inflow, the temperature in the reaction vessel was kept at 80° C. for 30 minutes for polymerization of the polymer (the second polymer for the first time). Subsequently, a mixture solution of 11.2 g of methyl methacrylate, 67.2 g of butyl acrylate, 40.0 g of butyl methacrylate, 16.0 g of acrylic acid, 16.0 g of methacrylic acid, 9.6 g of diacetone acrylamide, 1.6 g of n-dodecyl mercaptan, 110.0 g of ion-exchanged water, 3.2 g of 25% aqueous solution of AQUALON KH-10, and 24.0 g of 2% aqueous solution of ammonium persulfate was flowed into the reaction vessel from a dripping tank over a time period of 40 minutes, while keeping the temperature in the reaction vessel at 80° C. during inflow. After completion of the inflow, the temperature in the reaction vessel was kept at 80° C. for 30 minutes, and then 10.4 g of 25% aqueous ammonia was added for polymerization of a polycarbonyl compound portion having the same composition as in the Production Example 2-2.

Subsequently, a mixture solution of 67.2 g of methyl methacrylate, 83.2 g of butyl acrylate, 9.6 g of diacetone acrylamide, 0.08 g of n-dodecyl mercaptan, 161.9 g of ion-exchanged water, 3.2 g of 25% aqueous solution of AQUALON KH-10, and 24.0 g of 2% aqueous solution of ammonium persulfate was flowed into the reaction vessel from a dripping tank over a time period of 40 minutes, while keeping the temperature in the reaction vessel at 80° C. during inflow. After completion of the inflow, the temperature in the reaction vessel was kept at 80° C. for 60 minutes for polymerization of the polymer (the second polymer for the second time). Subsequently the content was cooled to room temperature, with a pH adjusted to 7.5 with addition of 25% aqueous ammonia, and then subjected to filtration with a 100 mesh screen, so that a waterborne polymer dispersion A-2 having a solid content of 40.0% and an average particle diameter of 176 nm was obtained.

Example 2-1

To 100 g of the waterborne polymer dispersion (A-1) obtained by the method in Production Example 2-2, 3.85 g of 50% aqueous solution of the semicarbazide composition obtained by the method in Production Example 2-1 was added, stirred and mixed, and to the mixture, 5 g of CS-12 (made by JNC Corporation) was then added, thoroughly stirred, and mixed, so that a coating liquid formed of aqueous polymer composition was obtained. The coating liquid was applied to a thickness of about 100 μm at room temperature for film formation, which was dried at 23° C. for 1 week to make a coating film. The produced coating film was immersed in water for 1 week for measurement of the rate of change in mass before and after the immersion, resulting in 1.7 times the weight with an absorption of 70%. The coating film was transparent with only slight whitening.

Example 2-2

To 100 g of the waterborne polymer dispersion (A-2) obtained by the method in Production Example 2-3, 3.85 g of 50% aqueous solution of the semicarbazide composition obtained by the method in Production Example 2-1 was added, stirred and mixed, and to the mixture, 5 g of CS-12 (made by JNC Corporation) was then added, thoroughly stirred, and mixed, so that a coating liquid formed of aqueous polymer composition was obtained. The coating liquid was applied to a thickness of about 100 μm at room temperature for film formation, which was dried at 23° C. for 1 week to make a coating film. The produced coating film was immersed in water for 1 week for measurement of the rate of change in mass before and after the immersion, resulting in 1.35 times the weight with an absorption of 35%. The coating film was transparent with only slight blue tint.

Comparative Example 2-1

To 100 g of the waterborne polymer dispersion (A-1) obtained by the method in Production Example 2-2, 12.7 g of 8% aqueous solution of adipic acid dihydrazide was added, stirred and mixed, and to the mixture, 5 g of CS-12 (made by JNC Corporation) was then added, thoroughly stirred, and mixed to make a coating liquid. The coating liquid was applied to a thickness of about 100 μm at room temperature for film formation, which was dried at 23° C. for 1 week to make a coating film. The produced coating film was immersed in water for 1 week for measurement of the rate of change in mass before and after the immersion, resulting in 3.65 times the weight with an absorption of 265%. Further, the coating film was remarkably whitened.

Comparative Example 2-2

To 100 g of the waterborne polymer dispersion (A-2) obtained by the method in Production Example 2-3, 12.7 g of 8% aqueous solution of adipic acid dihydrazide was added, stirred and mixed, and to the mixture, 5 g of CS-12 (made by JNC Corporation) was then added, thoroughly stirred, and mixed to make a coating liquid. The coating liquid was applied to a thickness of about 100 μm at room temperature for film formation, which was dried at 23° C. for 1 week to make a coating film. The produced coating film was immersed in water for 1 week for measurement of the rate of change in mass before and after the immersion, resulting in 2.80 times the weight with an absorption of 180%. Further, the coating film was whitened.

The invention claimed is:

1. A method for producing a semicarbazide composition, wherein the composition comprises:
   a semicarbazide compound (A) having an amino group and a semicarbazide group;
   a semicarbazide compound (B-1) having a structure with a semicarbazide group substituted for the amino group of the semicarbazide compound (A);
   a semicarbazide compound (B-2) as a dimer of the semicarbazide compound (B-1); and
   a semicarbazide compound (B-3) as a trimer of the semicarbazide compound (B-1);
   the semicarbazide composition having an analysis area ratio (a) represented by the following expression (a) of 0.008% or more and 2% or less:

$$\text{Analysis area ratio (a)} = S_A/(S_A + S_{B-1} + S_{B-2} + S_{B-3}) \times 100 \quad \text{(a)}$$

wherein $S_A$, $S_{B-1}$, $S_{B-2}$, and $S_{B-3}$ represent peak areas of peaks derived from the semicarbazide compound (A), the semicarbazide compound (B-1), the semicarbazide compound (B-2), and the semicarbazide compound (B-3), respectively, in a chromatogram obtained by high performance liquid chromatography analysis of the semicarbazide composition; and
   wherein the method comprises:
   a reaction step of reacting a compound (C) having two or more isocyanate groups in the molecule with hydrazine or a hydrazine derivative in a solvent to obtain the semicarbazide composition, wherein in the reaction step,
   the solvent contains water, a water-soluble organic solvent, and a water-insoluble solvent; and
   the amount of the water-insoluble solvent relative to the total amount of the water-soluble organic solvent and the water-insoluble solvent is 30 mass % or more.

2. The method according to claim 1, wherein the ratio of the number of moles of the hydrazine or hydrazine derivative to the number of moles of the isocyanate groups of the compound (C) is 0.7 to 5 in the reaction step.

* * * * *